United States Patent
Oh et al.

(10) Patent No.: US 9,820,963 B2
(45) Date of Patent: Nov. 21, 2017

(54) COMPOSITION CONTAINING LIGNAN COMPOUND AS ACTIVE INGREDIENT FOR PREVENTING OR TREATING CANCER

(71) Applicant: KOREA RESEARCH INSTITUTE OF BIOSCIENCE AND BIOTECHNOLOGY, Daejeon (KR)

(72) Inventors: Sei Ryang Oh, Daejeon (KR); Yong Yeon Cho, Gyeonggi-do (KR); Hyung Won Ryu, Daejeon (KR); Cheol Jung Lee, Gyeonggi-do (KR); Hye Suk Lee, Gyeonggi-do (KR); Doo Young Kim, Daejeong (KR); Jung Hee Kim, Daejeon (KR); Kyung Seop Ahn, Daejeon (KR); Mee Hyun Lee, Gyeonggi-do (KR); Hyeong Kyu Lee, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 15/022,546

(22) PCT Filed: Nov. 8, 2013

(86) PCT No.: PCT/KR2013/010108
§ 371 (c)(1),
(2) Date: Mar. 16, 2016

(87) PCT Pub. No.: WO2015/037778
PCT Pub. Date: Mar. 19, 2015

(65) Prior Publication Data
US 2016/0228402 A1    Aug. 11, 2016

(30) Foreign Application Priority Data
Sep. 16, 2013 (KR) .......... 10-2013-0111392

(51) Int. Cl.
| | | |
|---|---|---|
| A61K 31/34 | (2006.01) | |
| A61K 36/898 | (2006.01) | |
| A61K 45/06 | (2006.01) | |
| A61K 31/36 | (2006.01) | |
| A61K 36/575 | (2006.01) | |
| A61K 31/05 | (2006.01) | |

(52) U.S. Cl.
CPC .............. *A61K 31/34* (2013.01); *A61K 31/05* (2013.01); *A61K 31/36* (2013.01); *A61K 36/575* (2013.01); *A61K 36/898* (2013.01); *A61K 45/06* (2013.01)

(58) Field of Classification Search
CPC ....... A61K 31/34; A61K 36/898; A61K 45/06
See application file for complete search history.

(56) References Cited

FOREIGN PATENT DOCUMENTS

KR    1999-0035470 A    5/1999

OTHER PUBLICATIONS

Khavari, P.A. Nature reviews, 2006, vol. 6, pp. 270-280.*
Cheol-Jung Lee et al., "Targeting of magnolin on ERKs inhibits Ras/ERKs/RSK2-signaling-mediated neoplastic cell transformation", Carcinogenesis, Sep. 12, 2013 (published online: joutnals.permissions©oup.com), pp. 432-441.
R. Balakumbahan et al., "Acores calamus: An overview" Journal of Medicinal Plants Research, 2010, vol. 4, No. 25, pp. 2740-2745.
Ah Young Jun et al., "Tetrahydrofurofuran-type lignans inhibit breast cancer-mediated bone destruction by blocking the vicious cycle between cancer cells, osteoblasts and osteoclasts", Investigational New Drugs, May 15, 2013 (Published online), pp. 1-13.
Ji Hyn Jeong et al., "Liquid chromatography-atmospheric pressure chemical ionization tandem mass spectrometry or the simultaneous determination of dimethoxyaschantin, dimethylliroresinol, dimethylpinoresinol, epimagnolin A, fargesin and magnolin in rat plasma", Biomedical Chromatography, 2011, vol. 25, pp. 879-889.
Eun-Kyung Kim et al., "Beneficial effect of Flos magnoliae extract on multiple low dose streptozotocin-induced type 1 diabetes developments and cytokine-induced B-cell damage", International Journal of Molecular Medicine, 2008, vol. 22, pp. 481-488.
Muhammad Saleem et al., "An update on bioactive plant lignans", Natural Product Reports, 2005, vol. 22, pp. 696-716.
Sanghyun Lee et al., "Anti-Oxidant Activities of Acanthopanax senticousus Stems and Their Lignan Components", Archives of Pharmacal Research, 2004, vol. 27, No. 1, pp. 106-110.
ISA/KR, International Search Report issued on Jun. 16, 2014 in International Application No. PCT/KR2013/010108, total 8 pages including translation.

* cited by examiner

Primary Examiner — Samira Jean-Louis
(74) Attorney, Agent, or Firm — Masuvalley & Partners

(57) ABSTRACT

The present invention relates to a pharmaceutical composition for preventing, ameliorating, or treating cancer. More specifically, the present invention relates to a pharmaceutical composition for preventing or treating cancer including a lignan compound having a specific chemical structure (Chemical Formula 1); a health functional food composition for preventing or ameliorating cancer including the lignan compound; and a method for preventing, ameliorating, or treating cancer using the composition.

Further, the present invention relates to a use of the lignan compound in the preparation of a pharmaceutical composition or a health functional food composition for preventing, ameliorating, or treating cancer.

9 Claims, 40 Drawing Sheets

FIG. 13B

COMPOSITION CONTAINING LIGNAN COMPOUND AS ACTIVE INGREDIENT FOR PREVENTING OR TREATING CANCER

This application is a national phase application under 35 U.S.C. §371 of International Application Serial No. PCT/KR2013/010108 filed on Nov. 8, 2013, and claims the priority under 35 U.S.C. §119 to Korean Patent Application No. 10-2013-0111392, filed on Sep. 16, 2013, which are hereby expressly incorporated by reference in their entirety for all purposes.

TECHNICAL FIELD

The present invention relates to a pharmaceutical composition for preventing, ameliorating, or treating cancer. More specifically, the present invention relates to a pharmaceutical composition for preventing or treating cancer including lignan compound having a specific chemical structure (Chemical Formula 1); a health functional food composition for preventing or ameliorating cancer including the lignan compound; and a method for preventing, ameliorating, or treating cancer using the composition.

Further, the present invention relates to a use of the lignan compound in the preparation of a pharmaceutical composition or a health functional food composition for preventing, ameliorating or treating cancer.

BACKGROUND ART

Currently, cancer is one of the diseases with the highest mortality rates worldwide. Whereas the age of cancer occurrence is decreased, the average life expectancy is gradually increased, and therefore, the incidence rate of cancer is predicted to increase even more. According to the Statistics in 2013 provided by the National Cancer Center of Korea (Status based on Statistics (Cancer Facts & Figures 2013), p. 18, 2013), the number of cancer patients registered with the Cancer Registry Statistics Division in Korea in 2010 was 202,053, and it was estimated to reach about 270 thousand in 2015.

On the other hand, lignan compounds, which collectively refer to substances formed by two molecules of n-phenylpropane by oxidative condensation, are substances that have a β, γ-dibenzylbutane structure as a basic frame. Lignan is known to be present in higher plants, such as whole grains, legumes, vegetables, fruits, and seeds, etc., in high concentrations in nature, and present in body fluids of animals including humans (Namba, T., Coloured Ilustration of Wakan-Yaku, Hoikusha Publishing, Osaka, 1980, Vol. II, 127-129; Tang, W and G. Eisenbrand, Chinese Drugs of Plant Origin, Springer-Verlag, Berlin, 1992, 639-646).

The research on the effects of lignan compounds has been conducted for a long time, and the effects of the lignan compound that have recently received attention may be antioxidant activities, anti-asthmatic effects, anti-inflammatory effects, etc. (Korean Patent Application Publication No. 10-1999-0035470; Sang-Hyun Lee, et al., Archives of Pharmacal Research, 2004, 27(2), 106-110). However, the research on the anticancer effects of lignan compounds are still insufficient, and specifically, the anticancer effects of lignan compounds having a specific chemical structure are hardly known.

Although lignan compounds have β, γ-dibenzylbutane as a basic frame, lignan compounds fall into quite a broad range, in which the compounds having a wide variety of structures according to substitution, addition, etc., are present. Therefore, lignan compounds inevitably show substantial differences in their properties according to their specific structures. Accordingly, the research on the property of the lignan compounds having specific structures is of utmost significance. In particular, the fact that some of the compounds with fatal toxicity, such as podophyllotoxin, also belong to lignin compounds supports the significance of the study.

DISCLOSURE OF INVENTION

Technical Problem

The present inventors have endeavored to find a candidate substance for an antitumor agent. As a result, they have found that a lignan compound having a specific chemical structure, and in particular, the lignan compound having a structure of Chemical Formula 1 described below, shows excellent anticancer effects, thereby completing the composition for preventing, ameliorating, or treating cancer using the compound.

Technical Solution

It is an object of the present invention to prevent, ameliorate, or treat cancer by inhibiting the proliferation of tumor cells using a lignan compound having a specific chemical structure (Chemical Formula 1).

Specifically, it is an object of the present invention to provide a pharmaceutical composition for preventing or treating cancer, including a compound of the following Chemical Formula 1 or a pharmaceutically acceptable salt thereof as an active ingredient.

[Chemical Formula 1]

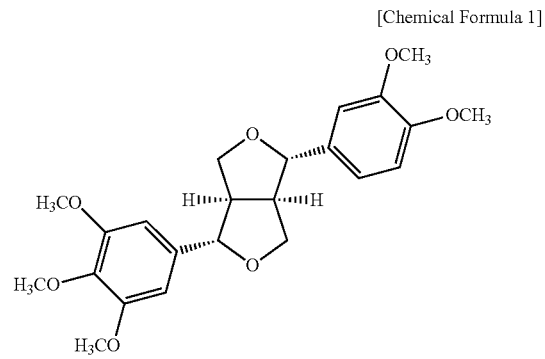 [SMILES: COc1ccc([C@H]2OC[C@H]3[C@@H]2CO[C@@H]3c2cc(OC)c(OC)c(OC)c2)cc1OC]

It is another object of the present invention to provide a health functional food composition for preventing or ameliorating cancer, including a compound of Chemical Formula 1 or a sitologically acceptable salt thereof as an active ingredient.

It is still another object of the present invention to provide a method for preventing, ameliorating, or treating cancer, including administering the composition to a subject.

It is still another object of the present invention to provide a use of the compound of Chemical Formula 1 or a pharmaceutically or sitologically acceptable salt thereof in the preparation of a pharmaceutical composition or a health functional food composition for preventing, ameliorating, or treating cancer.

Advantageous Effects

In the present invention, the compound of Chemical Formula 1 plays a role in inhibiting growth and/or proliferation of cells, and cancer may be prevented and treated effectively using the compound. Further, when the compound of Chemical Formula 1 is obtained from plants in nature for use, the compound can be used with increased safety, without requiring a serious stimulation or causing a harmful action in the body, in addition to the anticancer effects, since the compound is derived from a natural product.

BRIEF DESCRIPTION OF DRAWINGS

FIGS. 2A to 2F show inhibitory effects of a *Magnoliae Flos* extract and *Magnoliae Flos* fractions on cell proliferation in MTS values, in which FIG. 2A shows the inhibitory effect by a *Magnoliae Flos* extract (total fraction), FIG. 2B shows the inhibitory effect by a hexane fraction, FIG. 2C shows the inhibitory effect by a chloroform fraction, FIG. 2D shows the inhibitory effect by an ethyl acetate fraction, FIG. 2E shows the inhibitory effect by a butanol fraction, and FIG. 2F shows the inhibitory effect by a water fraction.

FIGS. 8A to 8H show TOFMS analyses on the eight main ingredient substances, which have an inhibitory effect on cell proliferation in the *Magnoliae Flos* extract and fractions thereof, in which FIG. 8A shows the inhibitory effect by dimethylpinoresinol, FIG. 8B shows the inhibitory effect by magnolin, FIG. 8C shows the inhibitory effect by dimethylliroresinol, FIG. 8D shows the inhibitory effect by epieudesmin, FIG. 8E shows the inhibitory effect by epimagnolin, FIG. 8F shows the inhibitory effect by demethoxyaschantin, FIG. 8G shows the inhibitory effect by aschantin, and FIG. 8H shows the inhibitory effect by fargesin.

FIG. 9A and FIG. 9B show the inhibitory effect of magnolin on cell proliferation, in which FIG. 9A shows an inhibitory effect on cell proliferation according to magnolin concentrations and FIG. 9B shows the cytotoxicity of magnolin.

FIG. 10A and FIG. 10B show the effects of magnolin on cell cycle progression, in which FIG. 10A shows the distribution rates according to cell cycle phases of the cells treated with magnolin and FIG. 10B shows the number of cells treated with magnolin throughout cell cycle phases.

FIGS. 11A and 11B show the effects of magnolin on cell cycle progression induced by epidermal growth factor (hereinafter, EGF), in which FIG. 11A shows the distribution rates according to the cell cycle phases of the cells treated with magnolin and FIG. 11B shows the number of cells treated with magnolin according to cell cycle phases.

FIGS. 12A to 12F show the effects of magnolin, which selectively inhibits the ERKs/RSKs signaling pathway, in which FIGS. 12A to 12D and 12F show the results of Western blot, FIG. 12E shows the inhibition of cell proliferation in JB6 Cl41 cells individually treated with magnolin and PD98059, respectively, represented by MTS values.

FIGS. 13A to 13E relate to whether magnolin targets ERK1 and ERK2, in which FIG. 13A shows that ERK1-mediated phosphorylation of RSK2 (at Thr359/Ser363 and Thr577) is inhibited by magnolin, FIG. 13B shows computational docking results of magnolin with ERK1 and ERK2, FIG. 13C shows the $IC_{50}$ value of magnolin in ERK1 activity, FIG. 13D shows the $IC_{50}$ value of magnolin in ERK2 activity, and FIG. 13E shows the decrease of ERK2 binding to ATP-agarose beads according to the increase of magnolin.

FIGS. 14A to 14D show the inhibitory effects of magnolin on ATF1 and AP-1 transactivation activities, in which FIG. 14A shows that EGF-induced ATF1 phosphorylation at Ser63 is inhibited by magnolin, FIG. 14B shows that EGF-induced nuclear phospho-ATF1 protein level is decreased by magnolin, FIG. 14C shows that EGF-induced c-Jun phorphorylation at Ser63 and Ser73 and AP-1 transactivation activities are inhibited by magnolin, and FIG. 14D shows that the nuclear phospho-c-Jun, which has been increased by EGF, is decreased by magnolin.

FIGS. 16A to 16C show that magnolin inhibits the transformation of H226 cells having normal Ras-wt and that of A549 cells having $Ras^{G12V}$, in which FIG. 16A shows the inhibition on proliferation of H226 cells having normal Ras-wt and A549 cells having normal $Ras^{G12V}$ by b magnolin treatment, and FIGS. 16B and 16C show the number and the size of the colonies for H226 cells having normal Ras-wt and A549 cells having $Ras^{G12V}$ by magnolin treatment using an ECLIPSE Ti inverted microscope and the NIS-Elements AR (V. 4.0) computer software program.

FIGS. 17A to 17C show whether cell proliferation and cell transformation are inhibited when $Ras^{G12V}$-expressing NIH3T3 cells and mock-expressing NIH3T3 cells are treated with magnolin, in which FIG. 17A shows whether Ras is expressed in each cell, FIG. 17B shows the inhibitory effect of magnolin on cell proliferation for each cell, and FIG. 17C shows the number and the size of the colonies for NIH3T3 cells expressing $Ras^{G12V}$ and NIH3T3 cells expressing mock by magnolin treatment using the ECLIPSE Ti inverted microscope and the NIS-Elements AR (V. 4.0) computer software program.

BEST MODE FOR CARRYING OUT THE INVENTION

Figure 1:
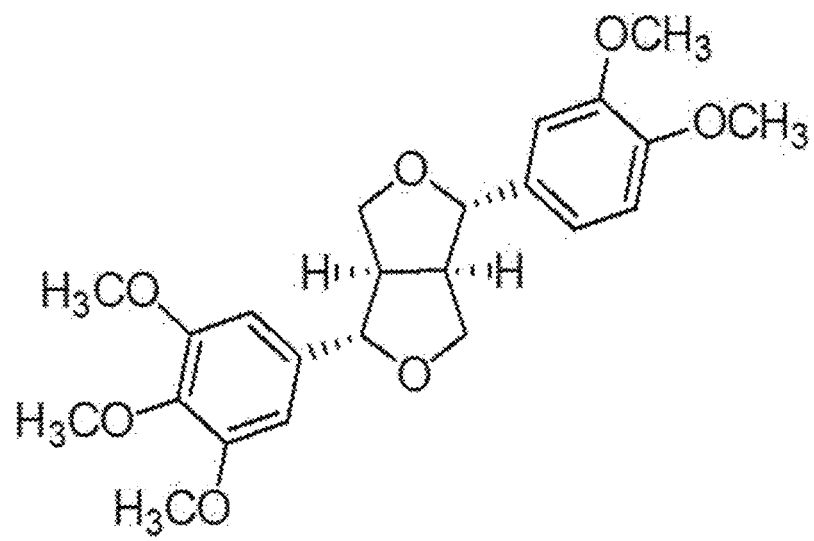
FIG. 1 shows a structure of a lignan compound (Chemical Formula 1) having an anticancer effect of the present invention.

In an aspect to achieve the above objects, the present invention provides a pharmaceutical composition for preventing or treating cancer, including a compound of the following Chemical Formula 1 or a pharmaceutically acceptable salt thereof as an active ingredient.

[Chemical Formula 1]

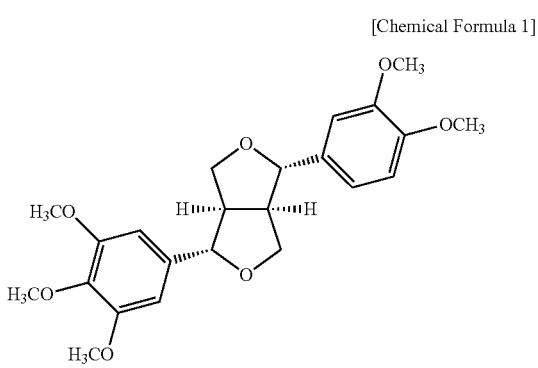 [SMILES: COc1ccc([C@H]2OC[C@H]3[C@@H]2CO[C@@H]3c2cc(OC)c(OC)c(OC)c2)cc1OC]

As used herein, the term "compound of Chemical Formula 1", which belongs to a lignan compound, may be prepared by one of ordinary skill in the art according to the known methods. For example, the compound of Chemical Formula 1 may be isolated and purified from the plants, which are known to contain the same in the technical field of the present invention, using a polar or non-polar solvent, or commercially available compounds may be purchased.

Regarding the compound of Chemical Formula 1 or the pharmaceutically acceptable salt thereof, the concentration of the compound of Chemical Formula 1 is not particularly limited as long as the composition can sufficiently exhibit the effects of preventing or treating cancer, but may be preferably in the range of from 1 μM to 100 μM, more preferably from 5 μM to 80 μM, and even more preferably from 10 μM to 70 μM, based on the volume of the composition. When the compound is within this range, there is an advantage in that cell growth and/or proliferation can be effectively inhibited. For reference, the "M" used in the concentration range of the compound of Chemical Formula 1 represents molarity, and the molarity represents the number of moles of solutes dissolved in 1 L of a solution.

As used herein, the term "pharmaceutically or sitologically acceptable salt" refers to all the salts (i.e., obtainable by reacting with acids or bases) of the compound of the present invention in which target animals (e.g., mammals) may accept physiologically. The salt of the compound of the present invention may be derived from organic or inorganic acids and bases. Examples of the acids may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methane sulfonic acid, ethane sulfonic acid, formic acid, benzoic acid, malonic acid, sulfonic acid, naphthalene-2-sulfonic acid, and benzenesulfonic acid, etc., but are not limited thereto. Although not being pharmaceutically or sitologically acceptable themselves, other acids, such as oxalic acid, etc., may be used in preparing useful salts as intermediates for obtaining the compounds of the present invention and pharmaceutically and sitologically acceptable addition salts. Examples of the bases may include alkali metal (e.g., sodium) hydroxide, alkaline earth metal (e.g., magnesium) hydroxide, and ammonia, but are not limited thereto. Examples of the salts may include acetate, adipate, alginate, aspartate, benzoate, benzenesulfonate, bisulfate, butyrate, citrate, camphorate, camphorsulfonate, cyclopentane-propionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfate, lactate, malate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and similar salts, but are not limited thereto. Other examples of the salts may include $Na^+$, $NH^{4+}$, and $NW^{4+}$ (in which W is a $C_{1-4}$ alkyl group), and anions of the compounds of the present invention compounded with suitable cations similar therewith. For use in preventing, ameliorating, or treating cancer, the salt of the compound of the present invention was considered to be pharmaceutically or sitologically acceptable. However, pharmaceutically or sitologically unacceptable salts of the acids and bases, for example, may also be used in the preparation or purification of pharmaceutically or sitologically acceptable compounds.

The composition including the compound of Chemical Formula 1 or pharmaceutically acceptable salt thereof of the present invention may further include one or more compounds selected from the group consisting of dimethylpinoresinol, dimethylliroresinol, epieudesmin, epimagnolin, demethoxyaschantin, aschantin, and fargesin. The compounds can exhibit excellent anticancer effects even when used alone and exhibit the anticancer effects without being used in combination with the compound of Chemical Formula 1.

As used herein, the terms "dimethylpinoresinol", "dimethylliroresinol", "epieudesmin", "epimagnolin", "demethoxyaschantin", "aschantin", and "fargesin", which belong to lignan compounds, may be prepared by one of ordinary skill in the art according to the known methods. For example, the compounds may be isolated and purified from the plants, which are known to contain the same in the technical field of the present invention, using a polar or non-polar solvent, or commercially available compounds may be purchased.

Examples of the structures of dimethylpinoresinol, dimethylliroresinol, epieudesmin, epimagnolin, demethoxyaschantin, aschantin, and fargesin used in the present invention are shown in Chemical Formulae 2 to 8 below.

[Chemical Formula 2]

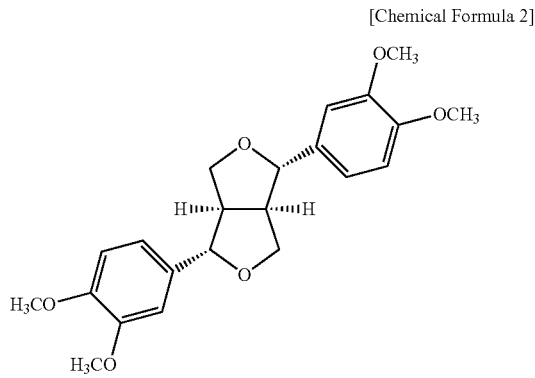

[Chemical Formula 3]

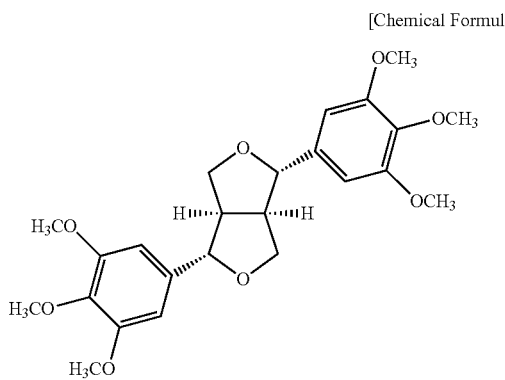

[Chemical Formula 4]

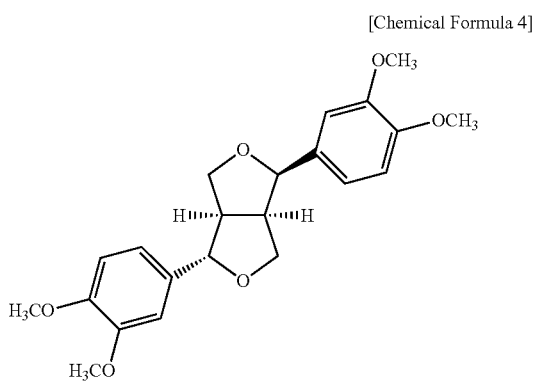

[Chemical Formula 5]

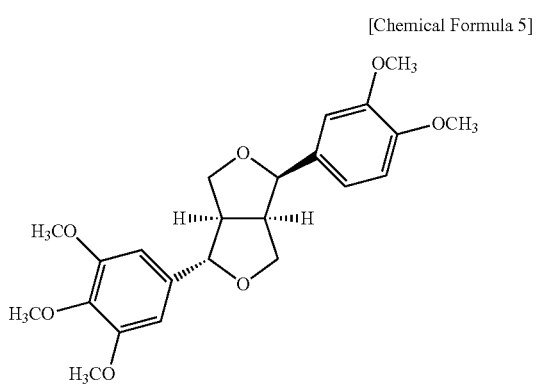

[Chemical Formula 6]

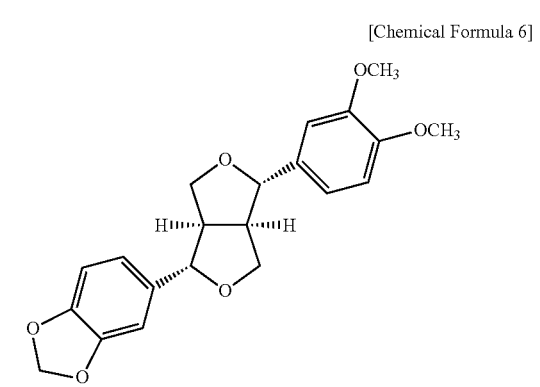

[Chemical Formula 7]

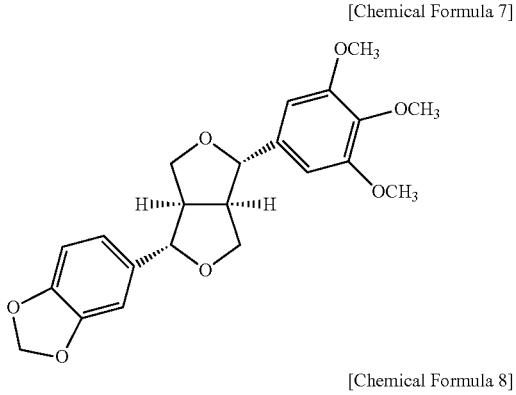

[Chemical Formula 8]

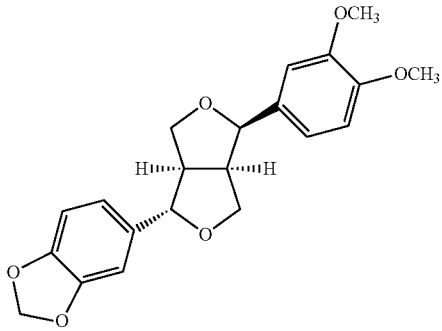

As used herein, the term "cancer", which is a disease related to the regulation of cell death, refers to a disease caused by hyperproliferation of cells when the balance for normal apoptosis is broken. In some cases, such abnormal hyperproliferative cells may invade surrounding tissues and organs to form a mass and thereby cause destruction or deformation of the normal structures in the body, and these conditions are collectively referred to as cancer.

In general, a tumor represents an abnormally-grown mass from an autonomous growth of body tissues, and may be classified into benign tumor and malignant tumor. A malignant tumor has a very rapid growth rate relative to a benign tumor, invades surrounding tissues, and causes metastasis, thus becoming life-threatening. Such malignant tumor is collectively referred to as 'cancer'.

In the present invention, cancer types are not particularly limited. The non-limiting examples of cancers may include spinal cord tumor, head and neck cancer, lung cancer, breast cancer, thymoma, mesothelioma, esophageal cancer, oral cavity cancer, colorectal cancer, liver cancer, stomach cancer, pancreatic cancer, biliary tract cancer, kidney cancer, bladder cancer, prostate cancer, testis cancer, germ cell tumor, ovarian cancer, uterine cervical cancer, endometrial cancer, lymphoma, acute leukemia, chronic leukemia, multiple myeloma, sarcoma, malignant melanoma, etc.

The composition of the present invention also shows effective anticancer effects on cancers other than the cancers described above, and is particularly effective for preventing or treating skin cancer and lung cancer. JB6 Cl41 cells used in an exemplary embodiment of the present invention are the representative cells to perform a transformation experiment for converting normal cells into cancer cells by stimulating epidermal growth factors (EGF, hereinafter) on the skin. A549 cells are the cells having a mutation on the constitutively active Ras as lung cancer cell lines in humans.

As used herein, the term "prevention" refers to all the activities, which inhibit or postpone the occurrence of cancer by administering the compound of Chemical Formula 1 or a pharmaceutically acceptable salt thereof of the present invention to a subject.

As used herein, the term "treatment" refers to all the activities by which the symptoms caused by cancer become improved or beneficially changed by administering the compound of Chemical Formula 1 or a pharmaceutically acceptable salt thereof of the present invention to the subject suspected of having the cancer.

In an exemplary embodiment of the present invention, the compound of Chemical Formula 1 or a pharmaceutically acceptable salt thereof of the present invention can prevent or treat cancer by inhibiting the proliferation of tumor cells. In a more specific exemplary embodiment of the present invention, it was confirmed that the compound of the Chemical Formula 1 inhibited the activity of extracellular signal-regulated kinase (ERK, hereinafter) by competing with ATP to bind to the active site of ERK, and the compound selectively inhibited the ERKs/RSKs signaling pathway and interrupted the cell cycle progression, thereby inhibiting cell proliferation (Examples 8 and 9).

The composition including the compound of Chemical Formula 1 or a pharmaceutically acceptable salt thereof of the present invention may further include pharmaceutically acceptable carriers and may be formulated with the carriers to be provided as foods, medicines, feed additives, and drinking water additives, etc. As used herein, the term "pharmaceutically acceptable carrier" refers to a carrier or a diluent, which does not irritate an organism and inhibit biological activity and property of the compound to be administered.

The types of the carriers that may be used in the present invention are not particularly limited, and any carriers may be used as long as they are conventionally used in the concerned technical field and are pharmaceutically acceptable. The non-limiting examples of the carriers may be saline solution, sterilized water, Ringer's solution, buffered saline solution, albumin injection solution, dextrose solution, maltodextrine solution, glycerol, ethanol, etc. They may be used alone or in combination of two or more types.

Further, if necessary, they may be used by adding other conventional additives, such as antioxidants, buffer solutions and/or bacteriostatic agents, etc., and may be formulated into injectable formulations, such as an aqueous solution, a suspension, and an emulsion, etc., pills, capsules, granules, tablets, etc., for use by adding a diluent, a dispersant, a surfactant, a binder, and/or a lubricant.

The method for administering the pharmaceutical composition for preventing or treating cancer including the compound of Chemical Formula 1 or a pharmaceutically acceptable salt thereof of the present invention is not particularly limited and may follow the methods used in the related art. The non-limiting examples of the administration methods may include oral administration or parenteral administration of the composition.

The pharmaceutical composition for preventing or treating cancer including the compound of Chemical Formula 1 or a pharmaceutically acceptable salt thereof may be formulated into a variety of formations according to the desired administration methods. The non-limiting examples of the oral administration formulations may include troches, lozenges, tablets, aqueous suspensions, oily suspensions, preparation powders, granules, emulsions, hard capsules, soft capsules, syrups, elixirs, etc.

For the preparation of the composition of the present invention into formulations for oral administration (e.g., tablets and capsules), binders such as lactose, saccharose, sorbitol, mannitol, starch, amylopectin, cellulose, gelatin, etc.; excipients such as dicalcium phosphate, etc.; disintegrants such as corn starch, sweet potato starch, etc.; and lubricants such as magnesium stearate, calcium stearate, sodium stearyl fumarate, polyethylene glycol wax, etc., may be further included. Further, for the capsule formulation, liquid carriers such as fatty oil, etc., may be further included in addition to the above-mentioned substances.

As the method for the parenteral administration of the composition of the present invention, for example, intravenous administration, intraperitoneal administration, intramuscular administration, subcutaneous administration, topical administration, etc., may be used. The method for spreading or spraying the composition may also be used, but the method is not limited thereto.

As for the formulations of the parenteral administration, for example, the composition may be formulated into injectable formulations, such as subcutaneous injection, intravenous injection, and intramuscular injection; suppository injection method; or sprays such as aerosol for inhalation through the respiratory tract, but is not limited thereto. For the preparation into the injectable formulations, the composition of the present invention may be mixed with a stabilizer or a buffer in water to be prepared as a solution or a suspension, and formulated into a unit-dose ampoule or vial. For the preparation of spray formulations such as aerosol, etc., propellants, etc., may be mixed with the additives so that waterborne concentrates or wetting powder may be dispersed.

A suitable spreading, spraying or administration dose of the pharmaceutical composition for preventing or treating cancer, including the compound of Chemical Formula 1 or a pharmaceutically acceptable salt thereof of the present invention may vary based not only on the formulation methods, administration methods, administration time and/or administration routes of the composition, but also based on age, weight, gender, severity of disease symptoms, food intake, excretion rate, etc., of the subject animals for the administration. One of ordinary skill in the art may readily determine and prescribe an effective administration dose for the desired treatment in the related art.

In another aspect of the present invention, the present invention provides a health functional food composition for preventing or ameliorating cancer, including a compound of the following Chemical Formula 1 or a sitologically acceptable salt thereof as an active ingredient.

[Chemical Formula 1]

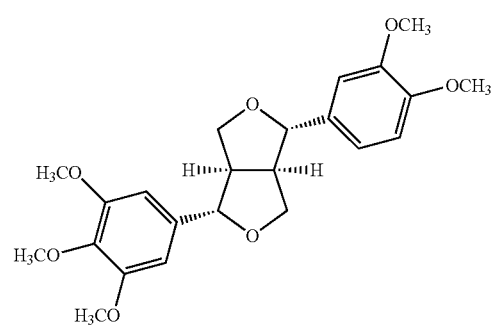

The composition of the present invention may further include one or more compounds selected from the group consisting of dimethylpinoresinol, dimethylliroresinol, epieudesmin, epimagnolin, demethoxyaschantin, aschantin, and fargesin.

As used herein, the term "improvement" refers to a parameter related to conditions being treated, for example, all the activities, which at least reduce the severity of symptoms.

When the health functional food composition of the present invention is used as food additives, the composition may be added as it is, or may be used with other foods or food ingredients, and may be used according to the conventional methods.

The types of the foods are not particularly limited and they include all the foods that can be considered within conventional meaning. The non-limiting examples of the foods to which the substances may be added may include meats, sausages, breads, chocolates, candies, snacks, cookies, pizzas, noodles, other noodles, gums, dairy products including ice creams, various soups, beverages, teas, drinks, alcoholic beverages, vitamin complexes, etc.

When the health functional food composition of the present invention is a beverage composition, flavoring agents or natural carbohydrates, etc., may be further included as additional ingredients, in addition to conventional beverages. The non-limiting examples of the natural carbohydrates may include monosaccharides, such as glucose and fructose; disaccharides, such as maltose and sucrose; natural sweeteners, such as dextrin and cyclodextrin; synthetic sweeteners, such as saccharin and aspartame, etc. The ratio of the additionally added ingredients may be appropriately determined by one of ordinary skill in the art.

In addition to those described above, the health functional food composition of the present invention may include various nutritional supplements, vitamins, electrolytes, flavoring agents, colorants, pectic acids and its salts, alginic acids and a salt thereof, protective colloidal thickeners, pH regulators, stabilizers, preservatives, glycerins, alcohols, carbonizing agents used for carbonated soft drinks, etc. In addition, the health functional food composition of the present invention may include fruit flesh for the preparation of natural fruit juices, fruit drinks, or vegetable drinks. These ingredients may be used alone or by combination of two or more kinds. The ratio of these additives may also be appropriately determined by one of ordinary skill in the art.

In still another aspect of the present invention, the present invention provides a feed additives or drinking water additives for preventing or ameliorating cancer, including the compound of Chemical Formula 1 or a pharmaceutically or sitologically acceptable salt thereof as an active ingredient.

The composition of the present invention may further include one or more compounds selected from the group consisting of dimethylpinoresinol, dimethylliroresinol, epieudesmin, epimagnolin, demethoxyaschantin, aschantin, and fargesin.

The feed additives or drinking water additives of the present invention may be used in such a manner that the composition including the compound of Chemical Formula 1 or a pharmaceutically or sitologically acceptable salt thereof is prepared independently in the form of a feed additive or drinking water additive and then mixed with the feed or drinking water, or in such a manner that the composition including the compound of Chemical Formula 1 or a pharmaceutically or sitologically acceptable salt thereof is directly added during the preparation of the feed or drinking water.

The feed additives or drinking water additives of the present invention may be in a liquid or dried state, and preferably in the form of dry powder. The drying method used for preparing the feed additives or drinking water additives as a dried powder form is not particularly limited, and the conventional methods used in the art may be used. The non-limiting examples of the drying methods may be blow-drying, air-drying, spray-drying, freeze-drying, etc. These may be performed by the method of using it alone or combining two or more methods.

The feed additives or drinking water additives of the present invention may further include other additives, if necessary. The non-limiting examples of the usable additives may include binders, emulsifiers, and preservatives, etc., for preventing the deterioration of the feed or drinking water; amino acid agents, vitamins, enzyme supplements, probiotics, flavoring agents, non-protein nitrogen compounds, silicate agents, buffers, colorants, extracting reagents, oligosaccharides, etc., for increasing the use of the feed or drinking water, and may further include other feed mixtures, etc. They may be used alone or two or more kinds of additives may be added together.

In still another aspect of the present invention, the present invention provides a feed or drinking water for preventing or ameliorating cancer, including the compound of Chemical Formula 1 or a pharmaceutically or sitologically acceptable salt thereof.

The composition of the present invention may further include one or more compounds selected from the group consisting of dimethylpinoresinol, dimethylliroresinol, epieudesmin, epimagnolin, demethoxyaschantin, aschantin, and fargesin.

The feed or drinking water may be prepared by adding the feed additives or drinking water additives to the feed or drinking water or by directly adding the compound of Chemical Formula 1 or the composition including the compound of Chemical Formula 1 thereto.

In the present invention, the types of the feed are not particularly limited, and the conventional feed used in the art may be used. The non-limiting examples of the feed may be a vegetable feed, such as grains, root plants, by-products of food processing, algae, fibers, by-products of medicine manufacture, fats and oils, starch, gourds, by-products from food processing, etc.; and an animal feed, such as proteins, inorganic compounds, fats and oils, minerals, unicellular protein, zooplankton or food, etc. These may be used alone or in combination of two or more kinds.

In the present invention, the types of the drinking water are not particularly limited, and the conventional drinking water used in the art may be used.

In still another aspect of the present invention, the present invention provides a method for preventing or treating cancer, including administering the pharmaceutical composition containing the compound of Chemical Formula 1 or a pharmaceutically acceptable salt thereof into a subject in need thereof.

As used herein, the term "subject" refers to all mammals including humans having a cancer or having the risk of cancer development.

The method of prevention or treatment of the present invention specifically includes administering a pharmaceutically effective amount of the composition containing the compound of Chemical Formula 1 or a pharmaceutically acceptable salt thereof to a subject, which has a cancer or having the risk of cancer development. A suitable daily dose of the composition including the compound of Chemical Formula 1 or a pharmaceutically acceptable salt thereof may be appropriately determined by one of ordinary skill in the art within the scope of right medical judgment.

The specific and pharmaceutically effective amount of the composition including the compound of Chemical Formula 1 or pharmaceutically acceptable salt thereof for specific animals may be determined by considering not only types and degrees of the response to be achieved; age, weight, general health status, gender or diet of the subject, but also administration time, administration routes, excretion rate, treatment duration, etc., of the composition containing magnolin as an active ingredient, and may vary depending on the ingredients of other pharmaceutical compositions used in combination at the same or different times, as well as various factors and similar factors well-known in the medical field.

With respect to the method of prevention or treatment of the present invention, the administration routes and administration methods of the composition including the compound of Chemical Formula 1 or a pharmaceutically acceptable salt thereof are not particularly limited, and may follow any administration routes and administration methods as long as the composition including the compound of Chemical Formula 1 or a pharmaceutically acceptable salt thereof can reach the target site. Specifically, the composition including the compound of Chemical Formula 1 or a pharmaceutically acceptable salt thereof may be administered orally or in various parenteral routes. The non-limiting examples of the administering routes include oral-, rectal-, topical-, intravenous-, intraperitoneal-, intramuscular-, intraarterial-, percutaneous-, intranasal-, and inhalation administrations.

In still another aspect of the present invention, the present invention provides a method for preventing or ameliorating cancer, including administering a health functional food composition containing the compound of Chemical Formula 1 or a sitologically acceptable salt thereof as an active ingredient to a subject in need thereof.

In the present invention, the explanations on the health functional food composition, administration dose, administration methods, administration routes, etc., of the composition are the same as described above.

In still another aspect of the present invention, the present invention provides a method for preventing, ameliorating, or treating cancer, including administering feed, feed additives, drinking water or drinking water additives containing the compound of Chemical Formula 1 or a pharmaceutically or sitologically acceptable salt thereof as an active ingredient to a subject in need thereof.

In the present invention, the explanations on the feed, feed additives, drinking water or drinking water additives, the administration dose, administration methods, administration routes, etc., of the composition are the same as described above.

In still another aspect of the present invention, the present invention provides a use of the compound of Chemical Formula 1 or a pharmaceutically or sitologically acceptable salt thereof in the preparation of the pharmaceutical composition or heatlh functional food composition for preventing, ameliorating or treating cancer.

In another aspect of the present invention, the present invention provides a use of the compound of Chemical Formula 1 or pharmaceutically or sitologically acceptable salt thereof in the preparation of feed, feed additives, drinking water or drinking water additives for preventing, ameliorating or treating cancer.

In another aspect of the present invention, the present invention provides a pharmaceutical composition for preventing or treating cancer including a *Magnoliae Flos* extract or a fraction thereof containing magnolin as an active ingredient.

In another aspect of the present invention, the present invention provides a health functional food for preventing or ameliorating cancer including a *Magnoliae Flos* extract or fraction thereof containing magnolin.

As used herein, the term "magnolin", which is one of the ingredients contained in *Magnoliae Flos*, belongs to the compounds that can be extracted or fractioned from *Magnoliae Flos*.

Regarding the magnolin used in the present invention, the source of origin is not particularly limited, and the magnolin obtained by extraction of *Magnoliae Flos*, which can be conventionally acquired in the art, or that obtained by the preparation or other methods, may be used. The magnolin used in an exemplary embodiment of the present invention was supplied by the Korea Research Institute of Bioscience and Biotechnology (KRIBB) and the magnolin extracted from Chinese *Magnoliae forgesii* (Cheng, *M. biondii* Pamp.) was used.

In an exemplary embodiment, the magnolin used in the present invention may be the compound of the following Chemical Formula 1.

[Chemical Formula 1]

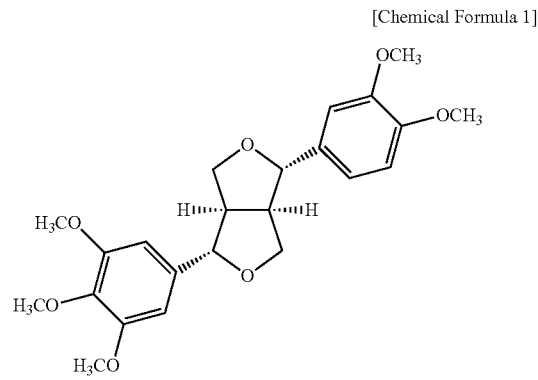 [SMILES: COc1ccc([C@H]2OC[C@H]3[C@@H]2CO[C@@H]3c2cc(OC)c(OC)c(OC)c2)cc1OC]

As used herein, the term "*Magnoliae Flos*" refers to dried *magnolia* buds, which belong to Magnoliaceae and have spicy taste. Since *Magnoliae Flos* is known to have the effects of wind-eliminating and freeing nasal cavity, it has been used as medicinal herbs, etc., from the old times. Regarding the *Magnoliae Flos* used in the present invention is any dried buds of *Magnolia*, which belong to the family Magnoliaceae, may be used without limitation, but preferably, dried Chinese *Magnoliae forgesii* buds yet to bloom may be used.

As used herein, the term "extract" refers to active ingredients isolated from a natural product. The extract includes the liquid extract itself and all the formulations that may be formed using the liquid extract, such as the liquid extract obtained from *Magnoliae Flos* extraction, a diluted or concentrated solution of the liquid extract, a dried product obtained by drying the liquid extract, a partially purified product or purified product of the liquid extract, or a mixture thereof, etc.

In the present invention, the method for extracting *Magnoliae Flos* is not particularly limited, and the extraction may be performed by the conventional methods used in the art. The non-limiting examples of the extraction methods may include ultrasonic extraction, filtration, and reflux extraction, etc.

In the present invention, the types of the solvents used for extracting *Magnoliae Flos* are not particularly limited and any solvent known in the art may be used. The non-limitingd examples of the extracting solvents may include water, alcohol, or a solvent mixture thereof. When alcohol is used as a solvent, more preferably, a low-grade $C_{1-4}$ alcohol may be used and even more preferably, methanol.

As used herein, the term "fraction" refers to a product obtained from the fraction for the purpose of isolating specific ingredients or a group of specific ingredients from the mixture containing various components.

In the present invention, the fractionation methods for obtaining the *Magnoliae Flos* fraction are not particularly limited and may be performed by the conventional method used in the art. In an exemplary embodiment of the present invention, a method in which the extract obtained from extracting *Magnoliae Flos* is treated with a predetermined solvent and the fraction is obtained from the extract is used. The types of the solvents for obtaining the *Magnoliae Flos* fraction are not particularly limited and any solvent known in the art may be used. The non-limiting examples of the solvent fractions may include polar solvents, such as water and alcohol; and non-polar solvents such as hexane, ethyl acetate, chloroform, dichloromethane, etc. These may be used alone or two or more kinds of the solvents may be mixed together for use. When alcohol is used among the solvents, a low-grade $C_{1-4}$ alcohol may be preferably used.

For the purpose of the present invention, more preferably, chloroform, hexane, and ethyl acetate may be used as the solvents for obtaining a *Magnoliae Flos* extract, and most preferably, chloroform.

Figure 2A:
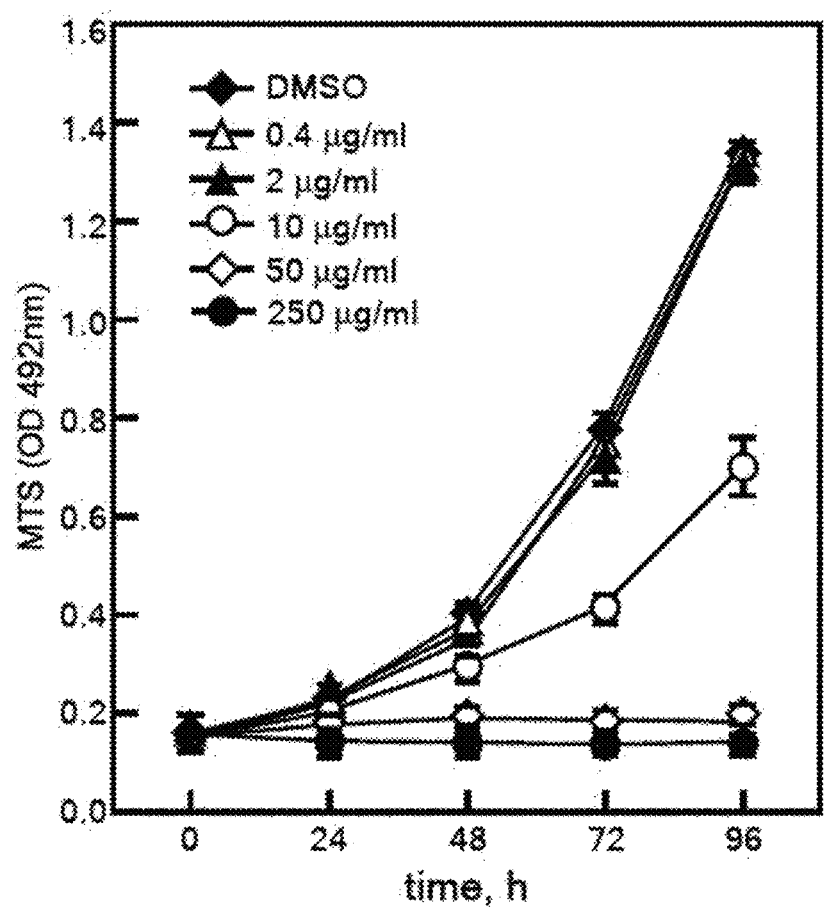
Figure 2B:
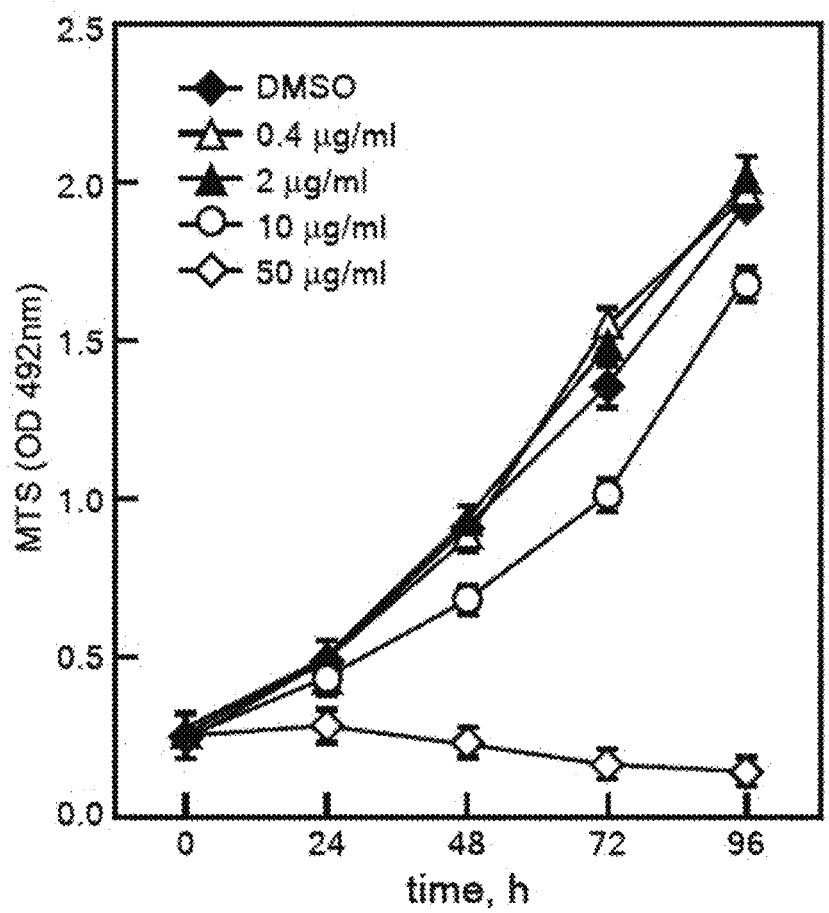
Figure 2C:
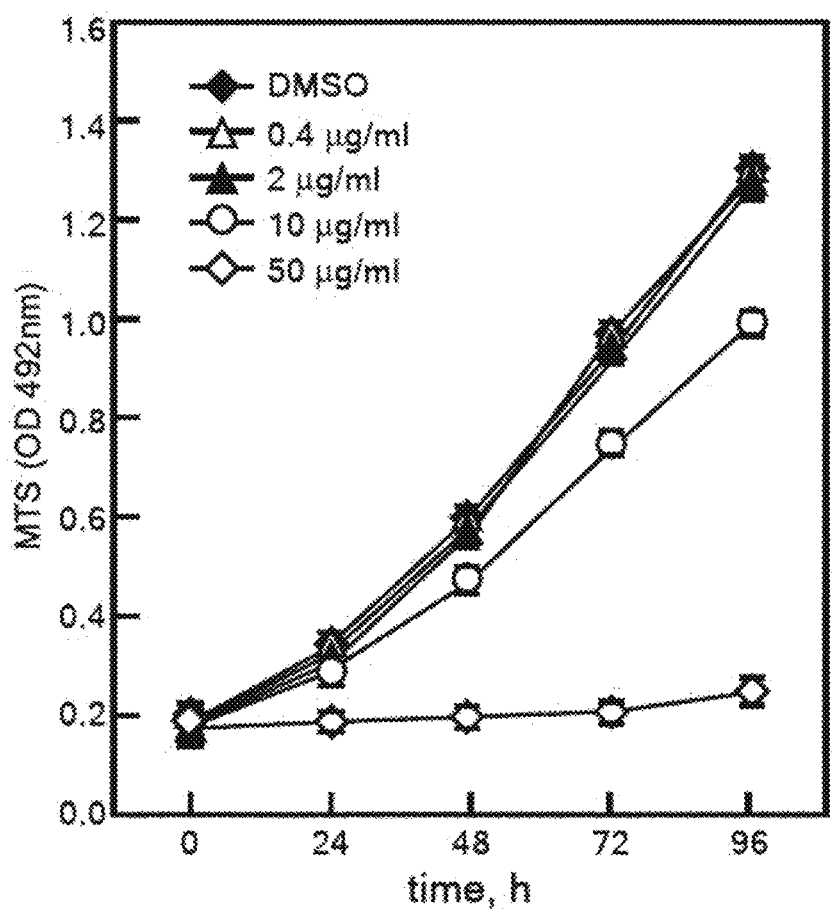
Figure 2D:
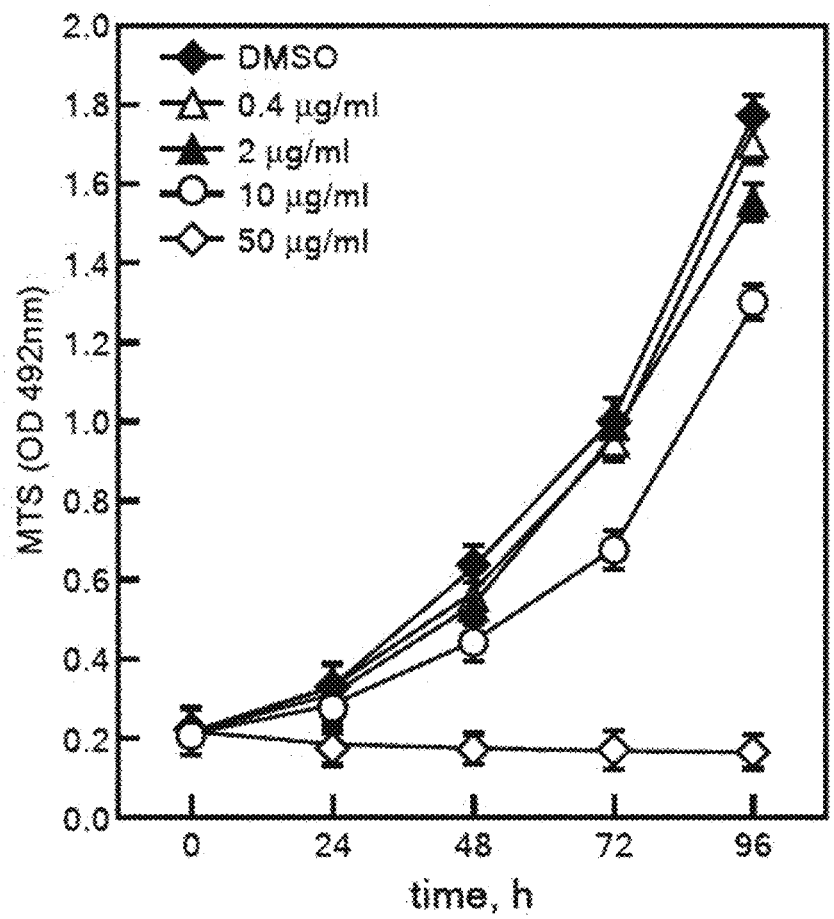
Figure 2E:
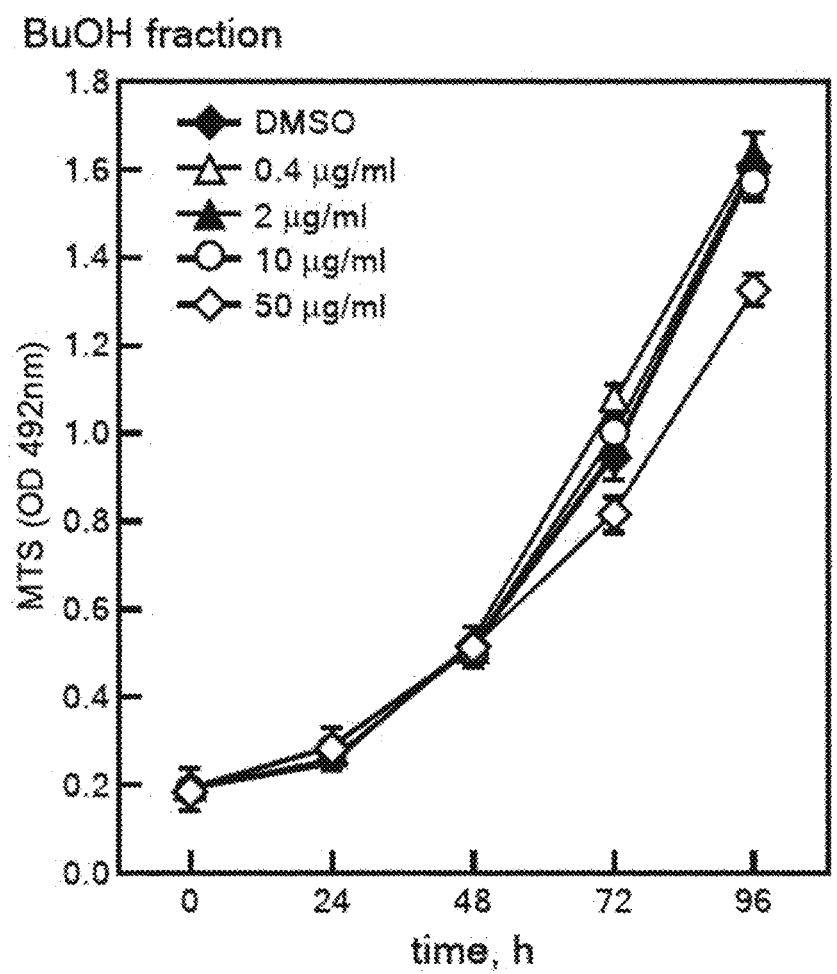
Figure 2F:
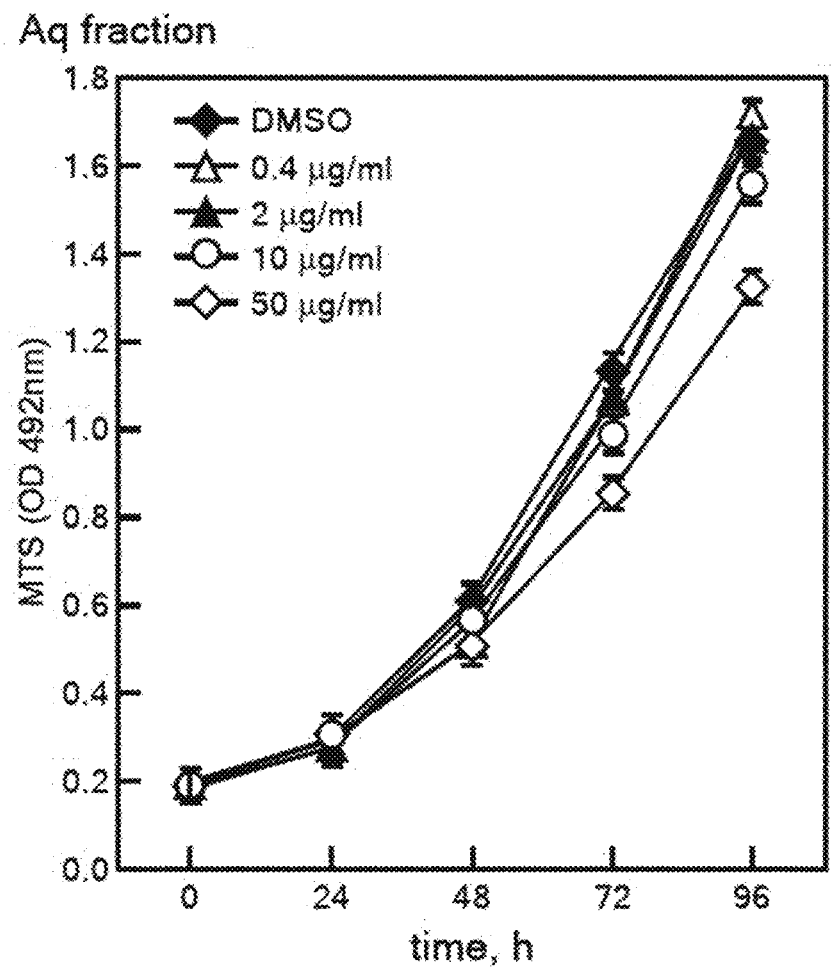

In an exemplary embodiment of the present invention, in which an MTS Assay was performed for various fractions of the *Magnoliae Flos* extract, specifically, a hexane fraction, a chloroform fraction, and an ethyl acetate fraction of the *Magnoliae Flos* fractions, were shown to effectively inhibit cell growth (FIGS. 2B to 2F). Additionally, the hexane fraction and the ethyl acetate fraction among the fractions showed a further decrease in MTS values when the cells were treated with about 50 μg/mL, compared to that at the initial 0 hour, i.e., before the cells were treated with the fractions (FIGS. 2B and 2D). On the contrary, the chloroform fraction showed no further decrease in MTS value compared to that at the 0 hour (FIG. 2C).

From these results, it was confirmed that all of the hexane fraction, the ethyl acetate fraction, and the chloroform fraction inhibited growth and/or proliferation of the cells and further, they were considered to cause cell death. However, for the hexane fraction and the ethyl acetate fraction, when treated at relatively high concentrations, the number of cells was considerably decreased compared to that at the initial 0 hour. Therefore, it was suggested that there was a possibility of causing not only the cell death by apoptosis, but also the cell death by necrosis.

That is, the factors inducing necrosis may be included in the hexane fraction and the ethyl acetate fraction. In this case, if necrosis can be controlled to selectively occur in cells inducing cancer occurrence or serious symptoms, such as tumor cells, it may be very effective for preventing and/or treating cancer. However, since necrosis is generally known to occur non-specifically in an unspecified number of cells, there is a concern for causing other side effects in addition to the inhibition of cancer cell growth and/or proliferation when the hexane fraction or the ethyl acetate fraction is used for cancer treatment at high concentrations. Therefore, it is preferable to conduct further research on this matter.

Accordingly, as described above, regarding the fraction of the *Magnoliae Flos* extract used in the present invention, the types of the solvents used for obtaining the fractions are not particularly limited, but, preferably, the fractions may be those obtained using hexane, ethyl acetate, or chloroform as solvents, and most preferably, the fractions may be those obtained using chloroform as a solvent.

The composition including the *Magnoliae Flos* extract or a fraction thereof containing magnolin as an active ingredient of the present invention may further include one or more compounds selected from the group consisting of dimethylpinoresinol, dimethylliroresinol, epieudesmin, epimagnolin, demethoxyaschantin, aschantin, and fargesin.

Regarding the composition including the *Magnoliae Flos* extract or a fraction thereof containing magnolin as an active ingredient of the present invention, the concentration of the *Magnoliae Flos* extract or a fraction thereof is not particularly limited as long as the composition sufficiently shows the effects of preventing or treating cancer, but preferably 2 μg/mL to 250 μg/mL, more preferably 5 μg/mL to 200 μg/mL, and even more preferably 10 μg/mL to 100 μg/mL, based on the volume of the composition. When the compound is within this range, there is an advantage in that cell growth and/or proliferation can be effectively inhibited, and additionally, excessive necrosis may be prevented when some of the ingredients contained in the *Magnoliae Flos* extract or a fraction thereof induce necrosis.

In an another aspect, the present invention provides a feed, feed additives, drinking water or drinking water additives, including a *Magnoliae Flos* extract or a fraction thereof containing magnolin as an active ingredient.

In the present invention, the explanations on the feed, feed additives, drinking water or drinking water additives are the same as described above.

In an another aspect, the present invention provides a method for preventing, ameliorating, or treating cancer, including administering the composition containing the *Magnoliae Flos* extract or a fraction thereof containing magnolin as an active ingredient to a subject in need thereof.

In the present invention, the explanations on the administration dose, administration methods, administration routes, etc., of the composition are the same as described above.

In still another aspect, the present invention provides a method for preventing, ameliorating, or treating cancer, including administering feed, feed additives, drinking water or drinking water additives containing the *Magnoliae Flos* extract or a fraction thereof containing magnolin as an active ingredient to a subject in need thereof.

In the present invention, the explanation about the feed, feed additives, drinking water or drinking water additives, and the explanations on administration dose, administration methods, administration routes, etc., of the composition are the same as described above.

In still another aspect, the present invention provides a use of the *Magnoliae Flos* extract or a fraction thereof containing magnolin in the preparation of a pharmaceutical composition or a health functional food for preventing, ameliorating, or treating cancer.

In still another aspect, the present invention provides a use of the *Magnoliae Flos* extract or a fraction thereof containing magnolin in the preparation of a feed, feed additives, drinking water or drinking water additives for preventing, ameliorating, or treating cancer.

MODE FOR CARRYING OUT THE INVENTION

Hereinafter, the present invention will be described in details with reference to the following Examples. However, these Examples are for illustrative purposes only, and the scope of the present invention is not limited to these Examples.

Preparation Example 1: Preparation of *Magnoliae Flos* Extract (Total Fraction)

For a *Magnoliae Flos* extract, Chinese *Magnoliae forgesii* (Cheng, *M. biondii* Pamp.) obtained from the Korea Plant Extract Bank at the Korea Research Institute of Bioscience and Biotechnology was used. The extract used was a *Magnoliae Flos* methanol extract obtained using methanol as a solvent.

The general extraction process of the extract is as follows. The *Magnoliae Flos* obtained was pulverized, powdered, and methanol was added thereto. The product was then extracted at room temperature, filtered, and subjected to evaporation under vacuum, and thereby the extract was obtained.

In order to examine the anticancer effects based on the extract concentrations, the extract was dissolved in dimethyl sulfoxide (DMSO, hereinafter, Sigma-Aldrich Co. LLC.) so that the solutions would be 1,000-fold higher concentrations than 0.4 µg/mL, 2 µg/mL, 10 µg/mL, 50 µg/mL, and 250 µg/mL, respectively. Each of the samples was stored at −20° C. In this Preparation Example, the reason for dissolving the extract in DMSO to have 1000-fold higher concentrations than the aforementioned concentrations is that the use of the 1000-fold-diluted DMSO, in which the extract is dissolved, enables the provision of the *Magnoliae Flos* extract of the aforementioned concentrations for the cells while adjusting the DMSO concentration provided along with the extract for the cells to be 0.1% or less so that the influence of DMSO on cell growth and proliferation can be minimized, in Examples described later.

Because the extract represents the fraction, which was not subjected to the fractionation process described later, the fraction may be considered as a "total fraction". Hereinafter, "*Magnoliae Flos* extract" and "total fraction" are understood to be used as the same meaning.

Preparation Example 2: Preparation of *Magnoliae Flos* Fraction

The *Magnoliae Flos* methanol extract (1.0 g) obtained in the Preparation Example 1 was added with 50 mL of distilled water and suspended therein. Then, an equal volume of n-hexane was added thereto and mixed, and the n-hexane soluble fraction portion and the water-soluble fraction portion were separated. After repeating the process three times, the fraction portions were filtered, concentrated under reduced pressure to obtain the hexane fraction an equal volume of chloroform was added to the remaining water layer, and the chloroform fraction was obtained in the same manner as described above. Then, the chloroform fraction was removed and an equal volume of ethyl acetate was added to the remaining water layer, and the ethyl acetate fraction was obtained in the same manner as described above. Then, the ethyl acetate fraction was removed and an equal volume of butanol was added to the remaining water layer, and the butanol fraction was obtained in the same manner as described above. Then, the butanol fraction was removed and the water fraction was obtained by concentrating the remaining water layer.

The thus-obtained hexane fraction, the chloroform fraction, the ethyl acetate fraction, and the butanol fraction were dissolved in DMSO so that they can be 1,000-fold higher concentrations of 0.4 mg/mL, 2 mg/mL, 10 mg/mL, 50 mg/mL, and 250 mg/mL, respectively. Each of the samples was stored at −20° C.

Example 1: Verification of the Inhibitory Effect of *Magnoliae Flos* Extract on Cell Proliferation (1) Cell Culture JB6 Cl41 mouse skin epidermal cells were cultured in minimum essential medium (MEM) containing 5% fetal bovine serum (FBS) at 37° C. in a 5% $CO_2$ bioreactor. The cells were subcultured at 80% to 90% confluence and the medium was changed every 2 to 3 days.

(2) Verification of the Inhibitory Effect of *Magnoliae Flos* on Cell Proliferation The cultured JB6 Cl41 cells ($1\times10^3$ cells) were aliquoted into 96-well plates and stabilized for 24 hours. Then, each well was added with 20 µL of an aqueous solution of 3-(4,5-dimethylthiazol-2-yl)-5-(3-carboxymethoxyphenyl)-2-(4-sulfophenyl)-2H-tetrazolium (MTS))-based Cell Titer 96 and cultured further for 1 hour at 37° C. in a 5% $CO_2$ bioreactor. The absorbance at 492 nm was measured to measure the growth of the cells at 0 hour.

While measuring the absorbance at 0 hour, the cells were simultaneously treated with the samples of the *Magnoliae Flos* extract (total fraction) according to the Preparation Example 1 to final concentrations of 0.4 µg/mL, 2 µg/mL, 10 µg/mL, 50 µg/mL, and 250 µg/mL, respectively (as described above, DMSO samples containing *Magnoliae Flos* extract were diluted 1,000-fold for use). The cells were cultured for 96 hours while measuring the absorbance at 24 hour intervals. The media containing the extract samples were changed every 24 hours.

In this Example, for the elimination of changes in absorbance caused by factors other than the cell number change, in order to confirm and correct the absorbance change by the fraction samples more accurately, the wells without cells were added with the same medium used for the cell treatment, and the absorbance was measured under the same condition and duration for the cell culture. The thus-obtained absorbance was excluded from the absorbance results obtained above and thereby the real absorbance based on the change in cell number was obtained. Further, cell culture was performed for cell culture, the cells were treated with DMSO, which was a control for the cells treated with each fraction sample.

As the result of the experiment, it was confirmed that the inhibitory effect of the *Magnoliae Flos* extract on cell proliferation was dependent on the concentration of the *Magnoliae Flos* extract. Specifically, when the concentration of the *Magnoliae Flos* extract was 0.4 µg/mL, cell proliferation was hardly inhibited. However, the *Magnoliae Flos* extract at a concentration of 2 µg/mL, showed a slight inhibition of cell proliferation, at a concentration of 10 µg/mL showed a considerable inhibition of cell proliferation, and at a concentration of 50 µg/mL and more, showed inhibition of the proliferation of almost all cells (FIG. 2A).

In light of the above experiment on the inhibitory effect of the *Magnoliae Flos* extract on cell proliferation, the maximum concentration of each of the fraction samples prepared according to the Preparation Example 2 for cell treatment was set at 50 µg/mL, and the following Examples were conducted.

Example 2: Verification of the Inhibitory Effect of *Magnoliae Flos* Extract on Cell Proliferation The experiment was conducted in the same manner as in Example 1 except that the cultured cells were treated with each of the fraction samples (the hexane fraction, the chloroform fraction, the ethyl acetate, the butanol fraction, and the water fraction) prepared according to the Preparation Example 2, in which the final concentrations were adjusted to 0.4 µg/mL, 2 µg/mL, 10 µg/mL, and 50 µg/mL, respectively, instead of treating with the *Magnoliae Flos* extract in Example 1.

As the result of the experiment, it was confirmed that the inhibitory effect of each of the *Magnoliae Flos* fractions on cell proliferation was dependent on the concentrations of *Magnoliae Flos* fractions, as is the case with the *Magnoliae Flos* extract. Specifically, when all the fraction samples were treated at the concentration of 2 µg/mL, a slight inhibitory effect on cell proliferation was observed, whereas the treatment with the samples at the concentration of 10 µg/mL, a noticeable inhibition on cell proliferation was observed. Additionally, when whereas the treatment with the samples at the concentration of 50 µg/mL, a considerable inhibitory effect on cell proliferation was observed, and specifically, the effects were excellent in the hexane fraction, the chloroform fraction, and the ethyl acetate fraction (FIGS. 2B to 2F).

In the case of the hexane fraction and ethyl fraction among the fractions, when the cells were treated with the hexane fraction at the concentration of 50 µg/mL, the MTS value was considerably lower than that measured at 0 hour, i.e., before the fraction treatment (FIGS. 2B and 2D). This suggests that a necrosis-inducing factor may be included in the hexane fraction and the ethyl acetate fraction. In this case, since necrosis may occur non-specifically in unspecified number of cells, more caution will be required to use the hexane fraction and the ethyl acetate fraction for cancer treatment.

For the chloroform fraction, unlike in the case of the hexane fraction and the ethyl acetate, the MTS value considerably decreased when treated with the chloroform fraction at the concentration of 50 µg/mL, but the MTS value did not go lower than the MTS value measured at 0 hour. Therefore, it was confirmed that the treatment with the chloroform fraction very effectively inhibited the cell proliferation without causing necrosis (FIG. 2C).

On the other hand, when comparing the treatment with the *Magnoliae Flos* extract to those with each of the *Magnoliae Flos* fractions, the inhibitory effect on cell proliferation was more excellent under the treatment with the *Magnoliae Flos* extract (total fraction) compared to those with each of the fractions, and specifically when treated at the concentration of 10 µg/mL. This suggests that there is a synergistic effect in the total fraction due to the combined inhibitory effects on cell proliferation through the hexane fraction, the chloroform fraction, the ethyl acetate fraction, the butanol fraction, and the water fraction. Table 1 below shows a summary of types and treatment concentrations of the fractions used in the Examples 1 and 2.

TABLE 1

| Fraction | Treatment concentration (µg/mL) |
| --- | --- |
| Total fraction | 0.4, 2, 10, 50, and 250 |
| Hexane fraction | 0.4, 2, 10, and 50 |
| Chloroform fraction | 0.4, 2, 10, and 50 |
| Ethyl acetate fraction | 0.4, 2, 10, and 50 |
| Butanol fraction | 0.4, 2, 10, and 50 |
| Water fraction | 0.4, 2, 10, and 50 |

Example 3: Verification of the Inhibitory Effect of the Chloroform Fraction of *Magnoliae Flos* on Cell Proliferation Based on the results of Example 2, in order to more thoroughly observe the inhibitory effect of the chloroform fraction on cell proliferation, which was considered to be particularly excellent for use in preventing or treating cancer, the chloroform fraction prepared in Preparation Example 2 was further fractionated into six fractions (chloroform #1 to #6) to conduct a further experiment.

To verify the inhibitory effect of the fractionated chloroform fractions on cell proliferation, the experiment was conducted in the same manner as in Example 2, except that the cultured cells were treated with the chloroform fraction samples #1 to #6.

Figure 3A:
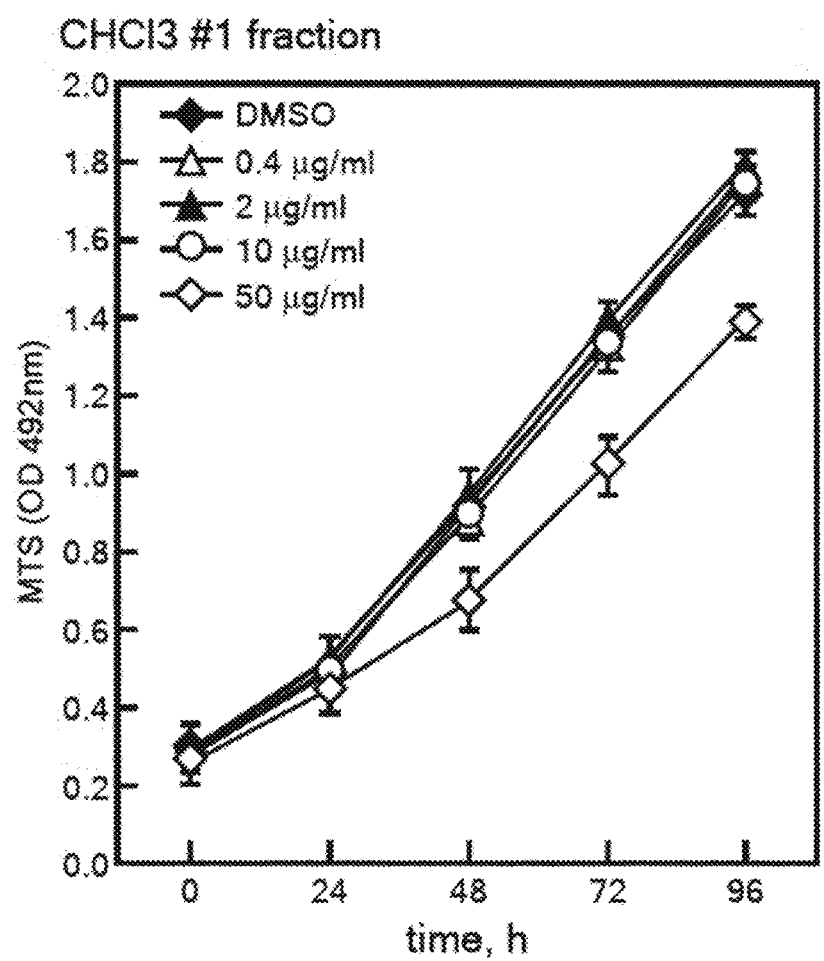
FIGS. 3A to 3F show the MTS values derived from the inhibitory effect of each of chloroform fractions on cell proliferation after further fragmenting the *Magnoliae Flos* chloroform fraction.
Figure 3B:
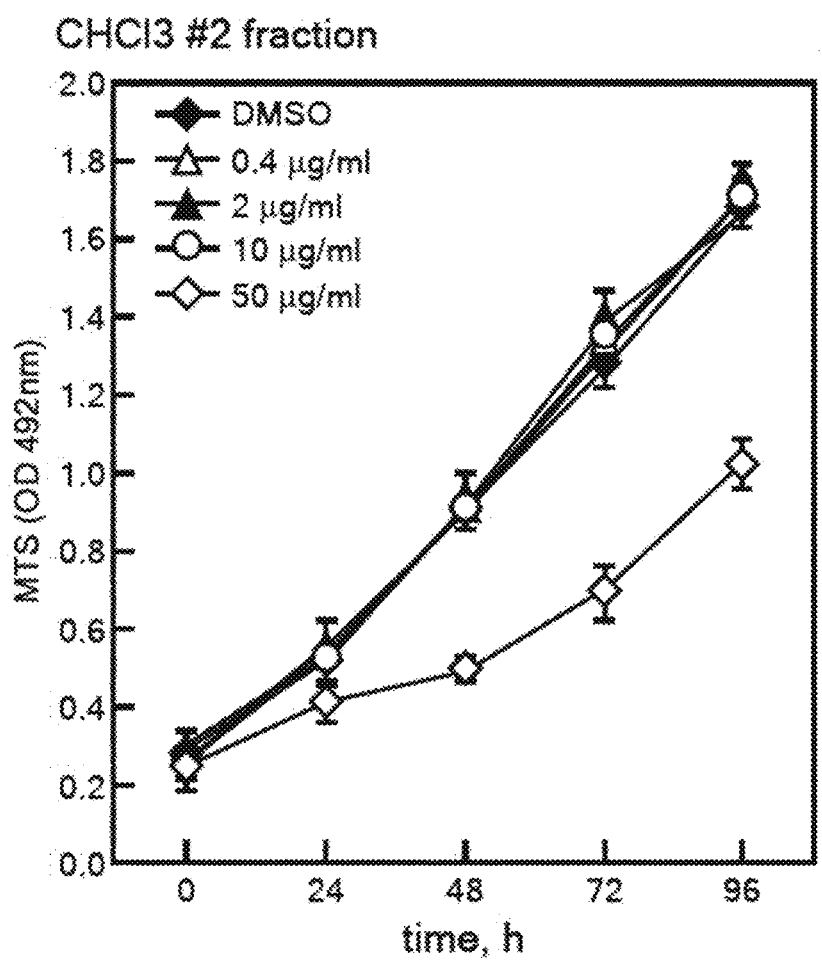
Figure 3C:
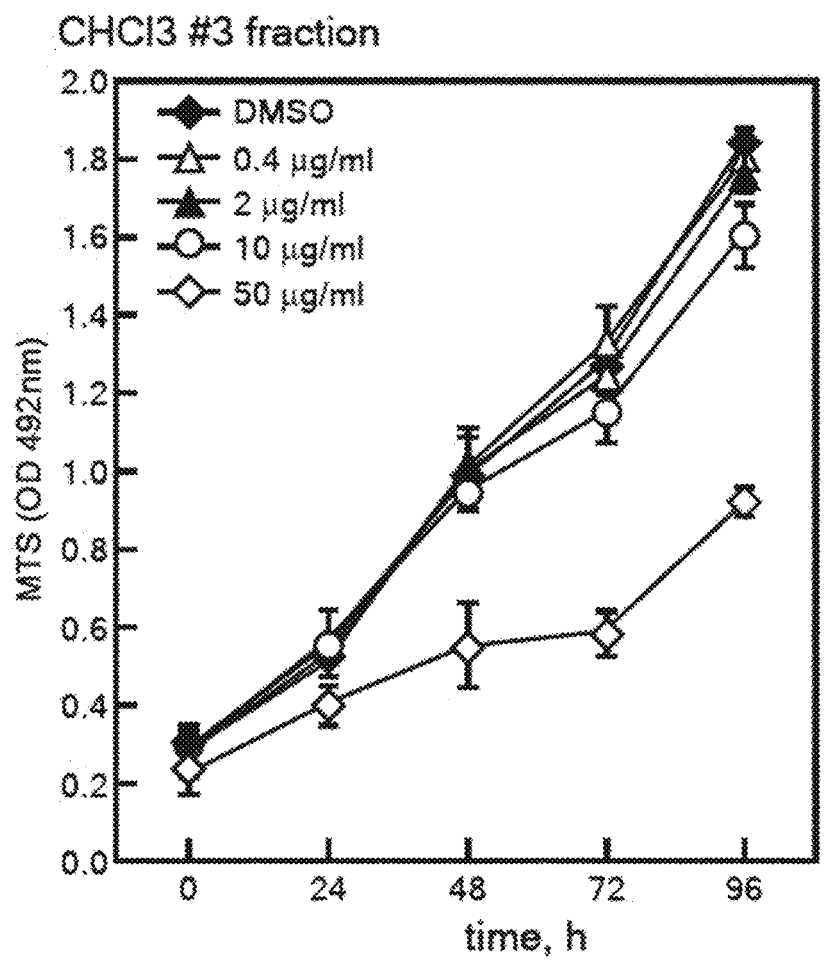
Figure 3D:
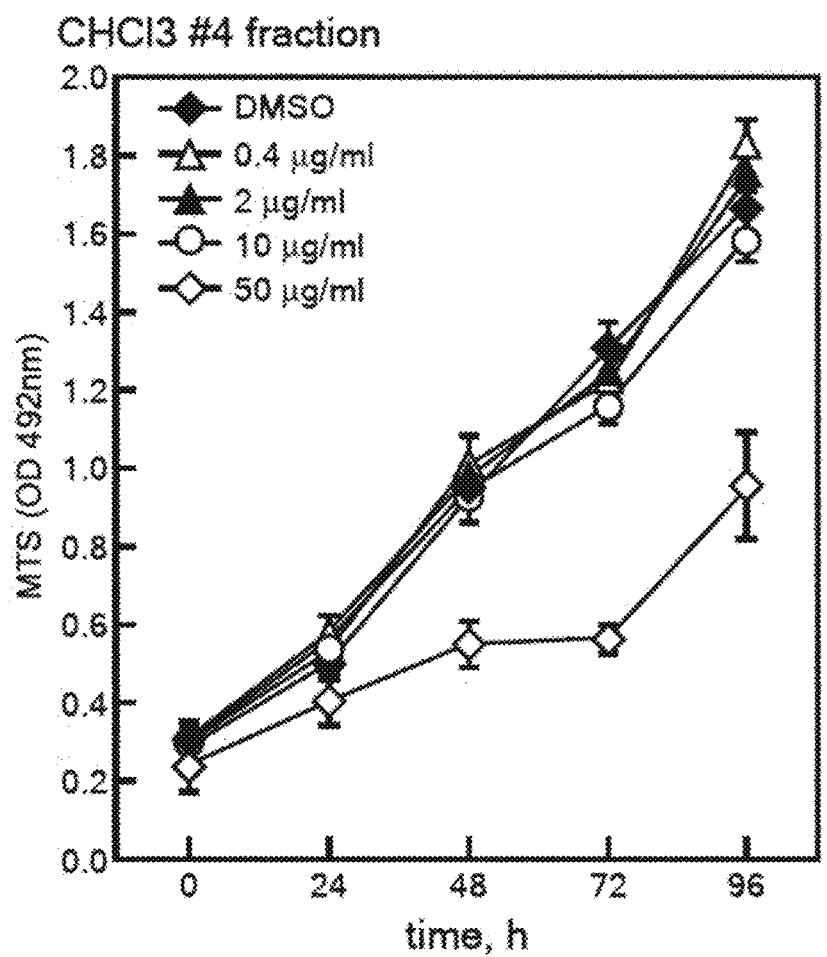
Figure 3E:
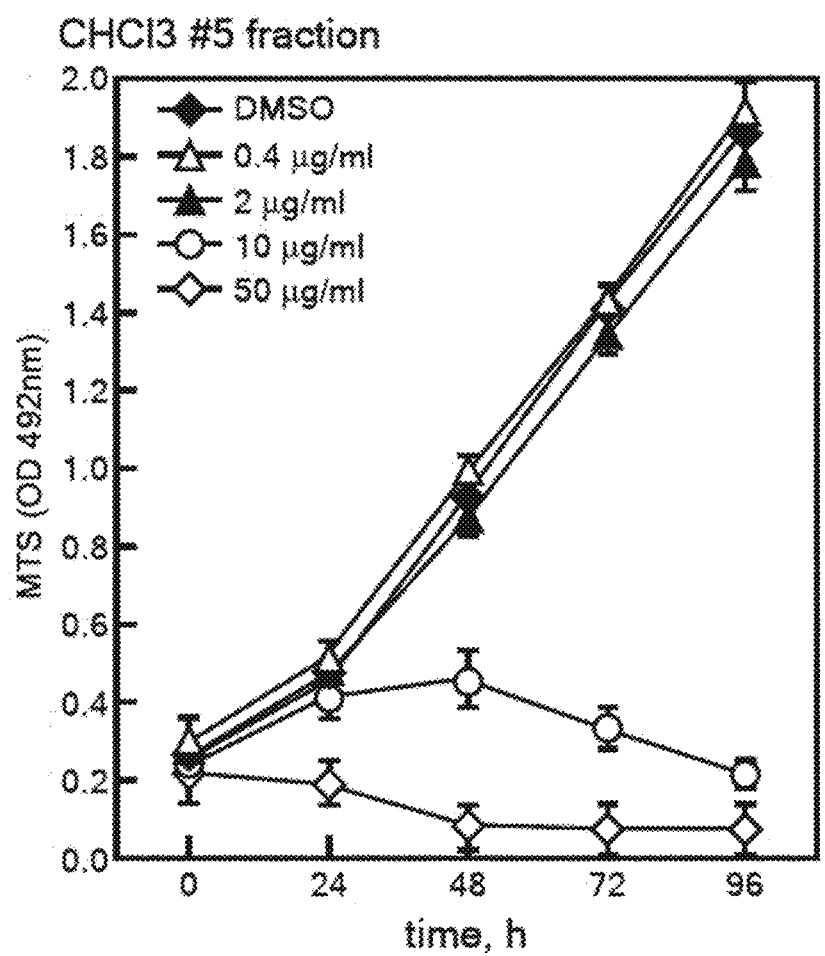
Figure 3F:
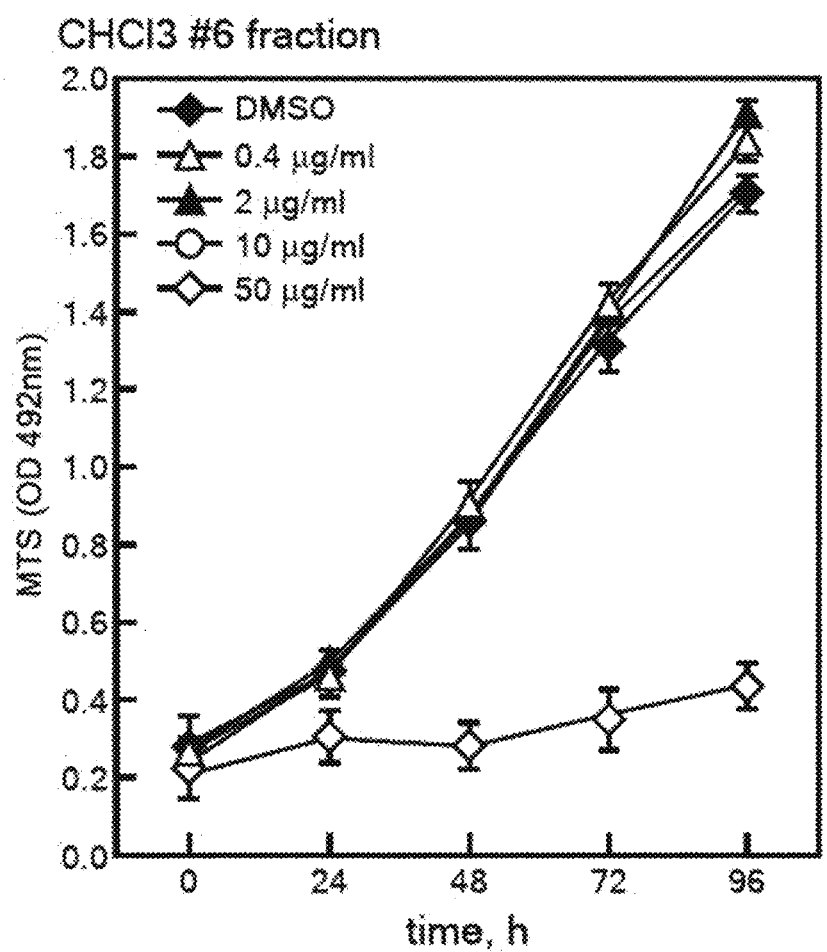

As the result of the experiment, it was confirmed that the chloroform fractions #2 to #6, among the chloroform fractions, specifically had excellent effects for the inhibition of cell proliferation, and in particular, the chloroform fractions #5 and #6 among them were particularly excellent (FIGS. 3B to 3F). However, for the chloroform fraction #5, when the cells were treated at the concentration of 50 µg/mL, the MTS value after about 48 hours was lower than that at 0 hour (FIG. 3E). Therefore, the subsequent experiment was conducted to confirm whether the decrease in the MTS values was caused by apoptosis or necrosis.

Example 4: Verification of the Effect of the Chloroform Fraction of *Magnoliae Flos* on Apoptosis Regarding the actions of the chloroform fractions #5 and #6, which had the highest inhibitory effect on cell proliferation in Example 3, the following experiment was conducted to confirm whether necrosis or apoptosis occurred.

JB6 Cl41 cells ($1 \times 10^5$ cells) were inoculated onto a cell culture dish with a diameter of 60 mm, cultured for 24 hours, and stabilized. The cells were treated with each of the chloroform fractions #5 and #6 at concentrations of 10 µg/mL and 50 µg/mL, respectively, and analyzed after 24 hours to examine the occurrence of apoptosis via fluorescence activated cell sorting (FACS) flow cytometry (BD FACSCalibur™, flow cytometry device, Franklin Lakes, N.J., USA). The chloroform fractions, which were treated on cells for the analysis of apoptosis and the culture media were collected together and the cells attached to the cell culture dish were separated by trypsinization and combined together. Then, the cells were obtained by centrifugation, suspended in phosphate buffered saline (PBS), treated with 20 µg/mL of propidium iodide (PI) and annexin V (Trevigen, Gaithersburg, Md., USA; diluted 100-fold for use), and reacted on ice for 15 minutes. Then, a washing process was repeated three times using PBS and the percentage of the cell population in which apoptosis occurred was confirmed via flow cytometry.

Figure 4:
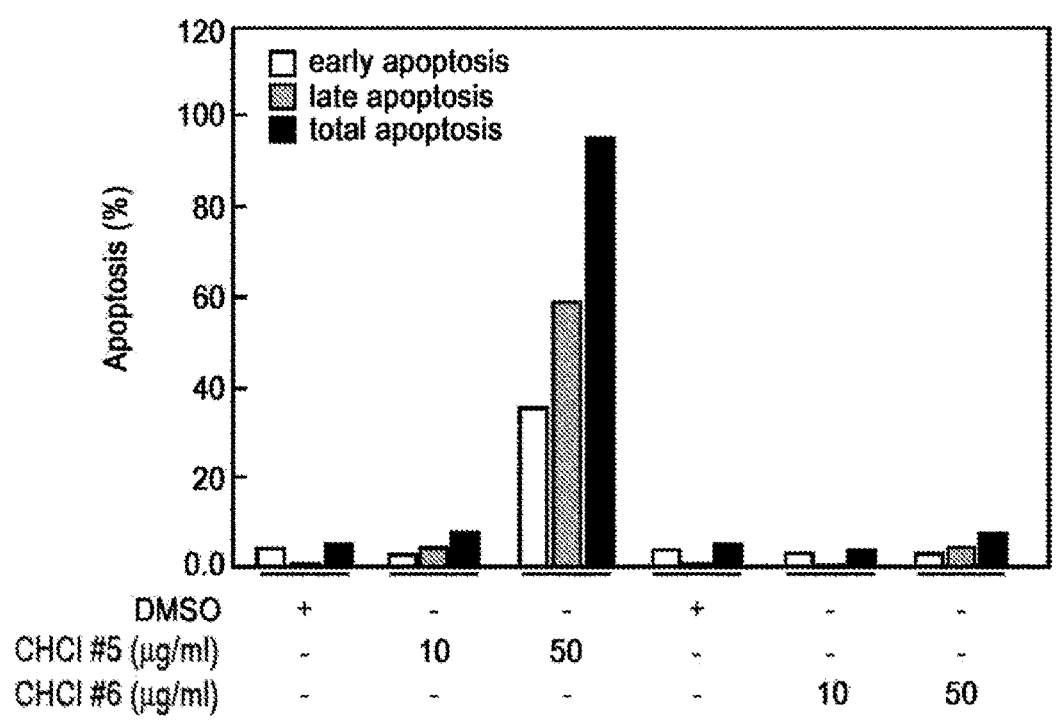
FIG. 4 shows the apoptotic effect according to types and concentrations of the chloroform fractions.
Figure 5:
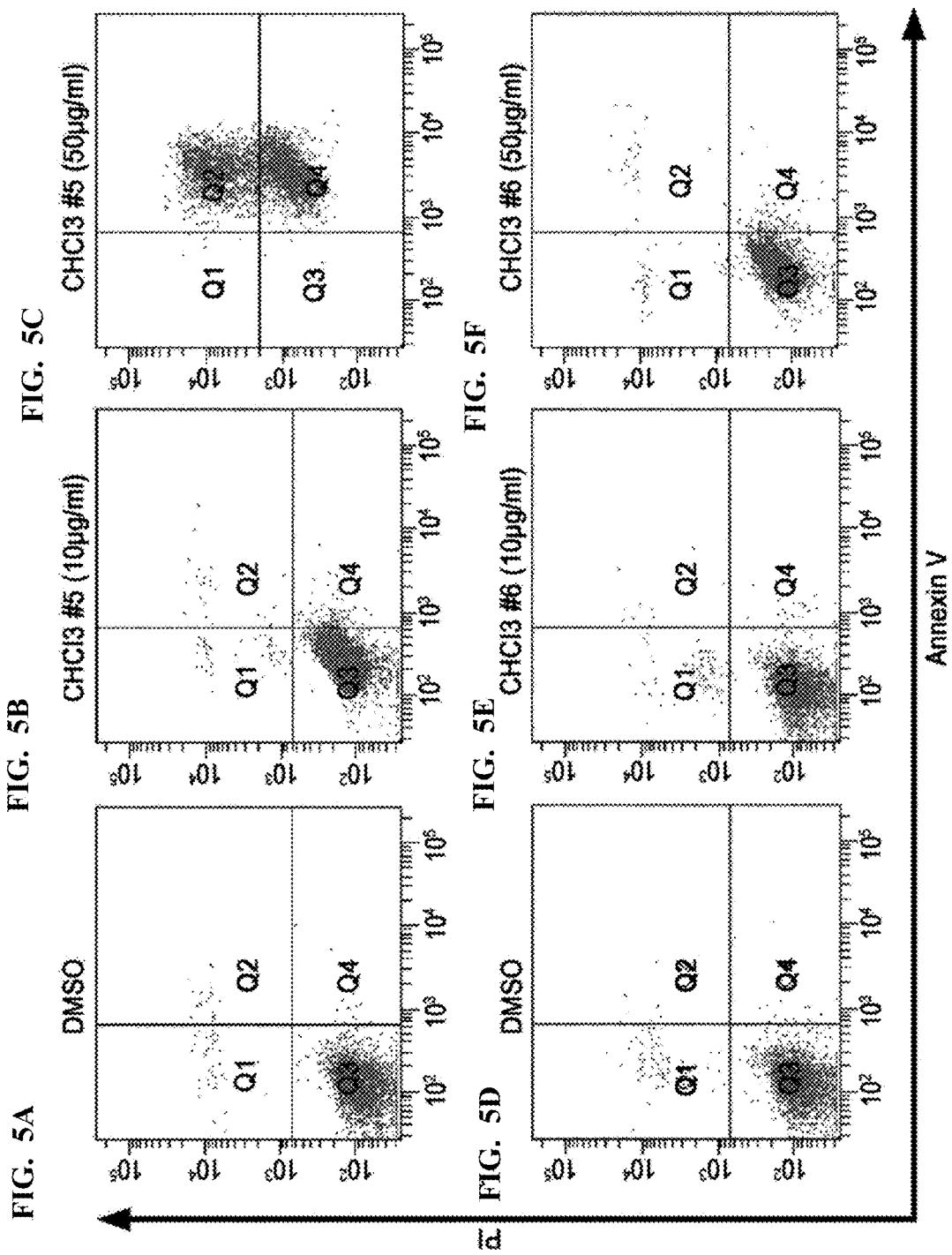
FIG. 5A to FIG. 5D show the apoptotic effect according to types and concentrations of the chloroform fractions through PI and annexin V staining.

As the result of the experiment, the chloroform fraction #5 at the concentration of 10 µg/mL showed an increase in the amount of annexin V compared to that of the DMSO control, but the occurrence of apoptosis sufficient for determining critical apoptosis was not observed (FIGS. 4, 5A, and 5B). However, in the case when the concentration of the chloroform fraction #5 was 50 µg/mL, the intensity of annexin V staining and PI staining simultaneously increased along with the increase of the phosphatidylserine staining concentration in the outer cell membrane and the PI staining concentration thus confirming the occurrence of apoptosis. It was confirmed that the sum of the early apoptosis due to the annexin V increase and the late apoptosis due to the PI staining increase had a significant apoptotic ability, which was enough to reach about 100% of the total cell population in 24 hours after the treatment with the chloroform fraction #5 (FIGS. 4 and 5C).

In contrast, the treatment with the chloroform fraction #6 at a concentration of 50 µg/mL, as observed in Example 3, was shown to significantly inhibit cell proliferation (FIG. 3F), and it was found that the annexin V staining level shown at 24-hour after the chloroform fraction #6 treatment moved slowly along with the concentration of annexin V (FIGS. 5D to F). The result suggests that the chloroform fraction #6 does not cause rapid apoptosis, but reduces cell proliferation.

Example 5: Analysis of Ingredients Contained in the *Magnoliae Flos* Extract and Fractions Thereof Based on the results of Examples 1 to 4, the experiment shown below was conducted to isolate the substances capable of inhibiting cell proliferation and inducing apoptosis among the substances contained in the *Magnoliae Flos* extract and fractions thereof and to analyze the structures thereof.

Pulverized *Magnoliae Flos* (3 kg) was added with 9 L of methanol, immersed for 3 days, extracted, re-extracted two more times using 5 L of methanol, all concentrated under reduced pressure, and the extract with a total amount of 225 g was obtained. The resulting extract was suspended in 2 L of distilled water, repeatedly extracted three times with 1 L of n-hexane, and, 40 g of the hexane fraction was obtained. Chloroform, ethyl acetate, and n-butanol were sequentially added to the remaining aqueous solution layer, respectively, and the chloroform fraction (109 g) was obtained. While increasing the polarity of the n-hexane-acetone solvent mixture, 100 g of the chloroform fraction was eluted using silica gel column chromatography (Kieselgel 60; No 9385, Merck), and 19 fractions were obtained therefrom.

An active mixture was isolated using the eighth fraction by reverse column chromatography (YMCgel ODS-4 60A; 70-230 mesh, YMC, elution; methanol:$H_2O$=7:3). Then, 400 mg of demethoxyaschantin, 260 mg of aschantin, and 59 mg of fargesin were isolated using HPLC (column; Capcell PAK C18; Φ20×250 mm, Shiseido, elution; methanol:acetonitrile:$H_2O$=3:2:5), respectively.

Further, in the eleventh fraction, 200 mg of dimethylpinoresinol, 720 mg of magnolin, 110 mg of dimethylliroresinol, 20 mg of epimagnolin, and 100 mg of epieudesmin were isolated using HPLC (column; Capcell PAK C18; Φ20×250 mm, Shiseido, elution; methanol: acetonitrile: $H_2O$=6:7:12), respectively, from the active mixture obtained from the reverse column chromatography (YMCgel ODS-4 60A; 70-230 mesh, YMC, elution; methanol:$H_2O$=3:2). For the respectively isolated compounds, the structures were analyzed using NMR and LC-MS, and the structures were identified by referring to the previously reported results of structural analysis.

Figure 6:
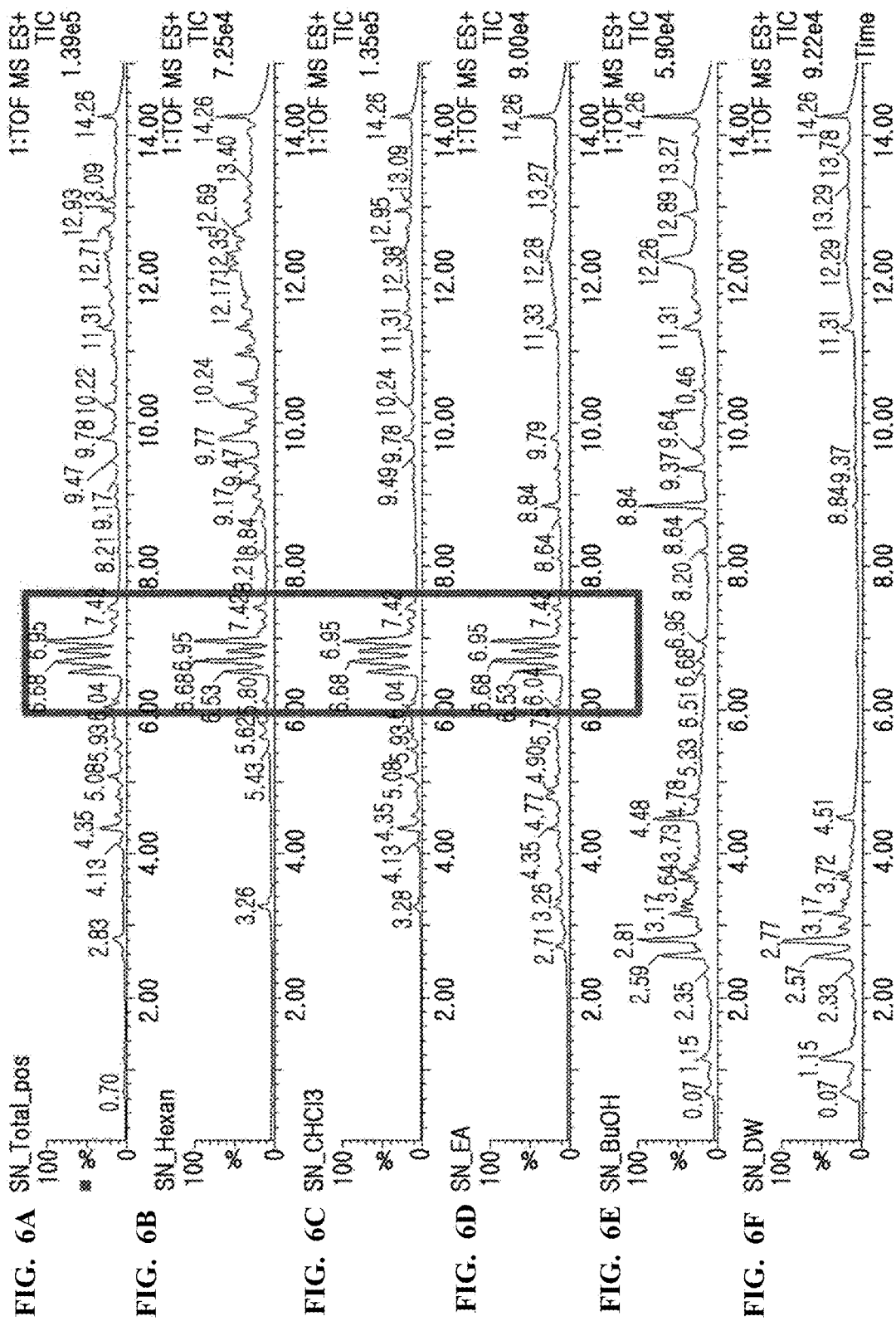
FIG. 6A to FIG. 6F show analyses of ingredient substances present in the *Magnoliae Flos* extract and fractions thereof.
Figure 7:
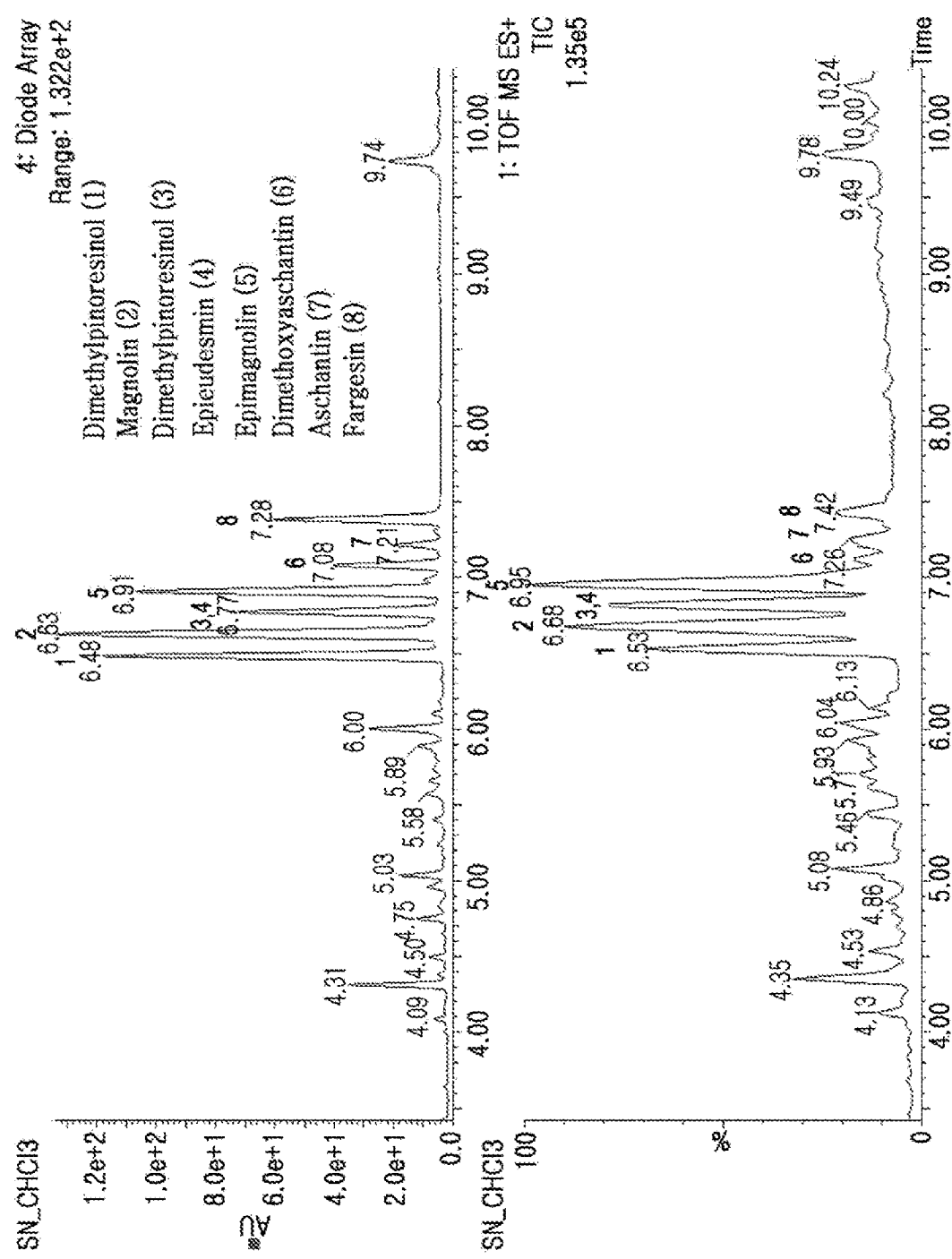
FIG. 7 shows the analyses of eight main ingredient substances, which have an inhibitory effect on cell proliferation, among the ingredients present in the *Magnoliae Flos* chloroform fractions.
Figure 8A:
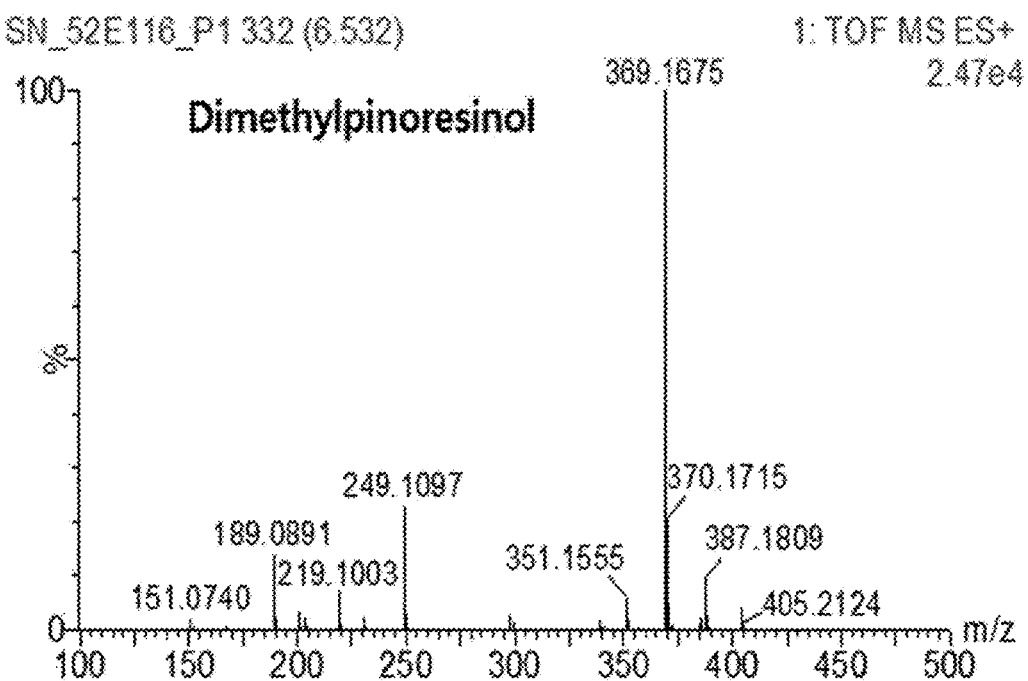
Figure 8B:
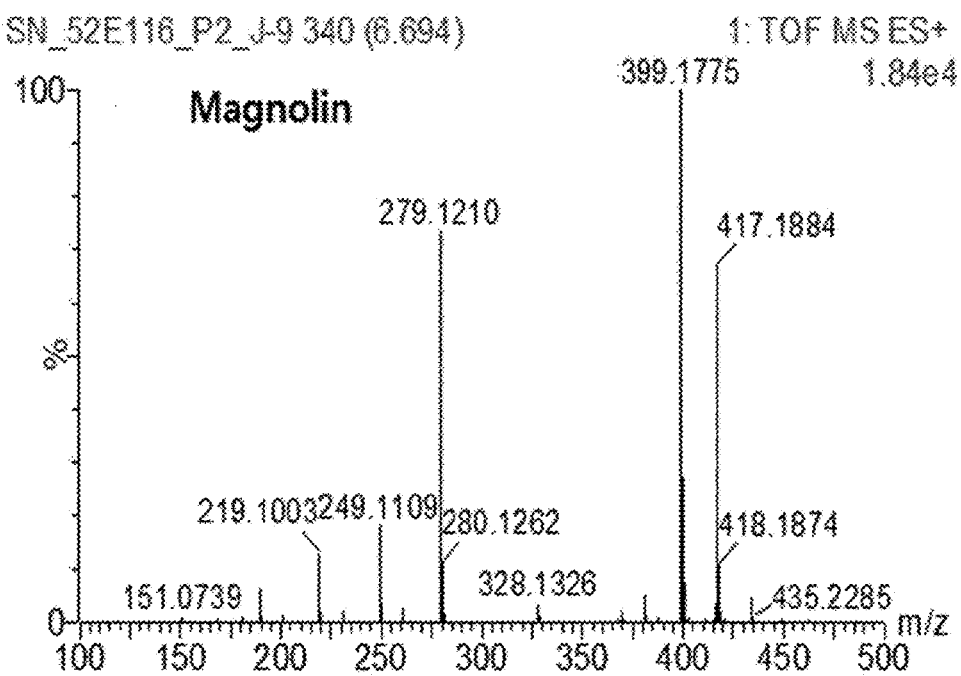
Figure 8C:
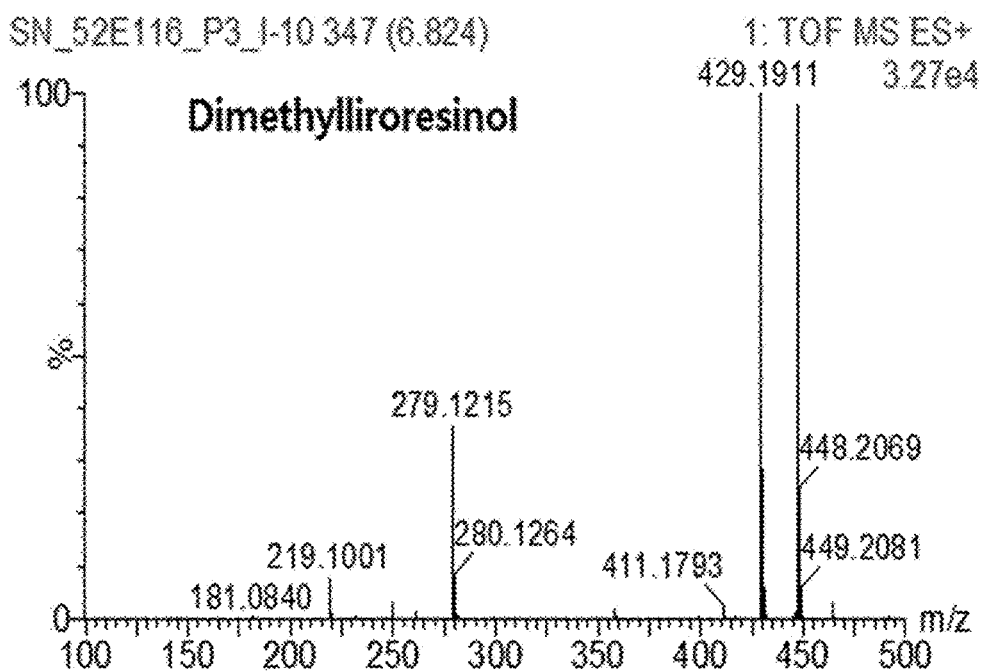
Figure 8D:
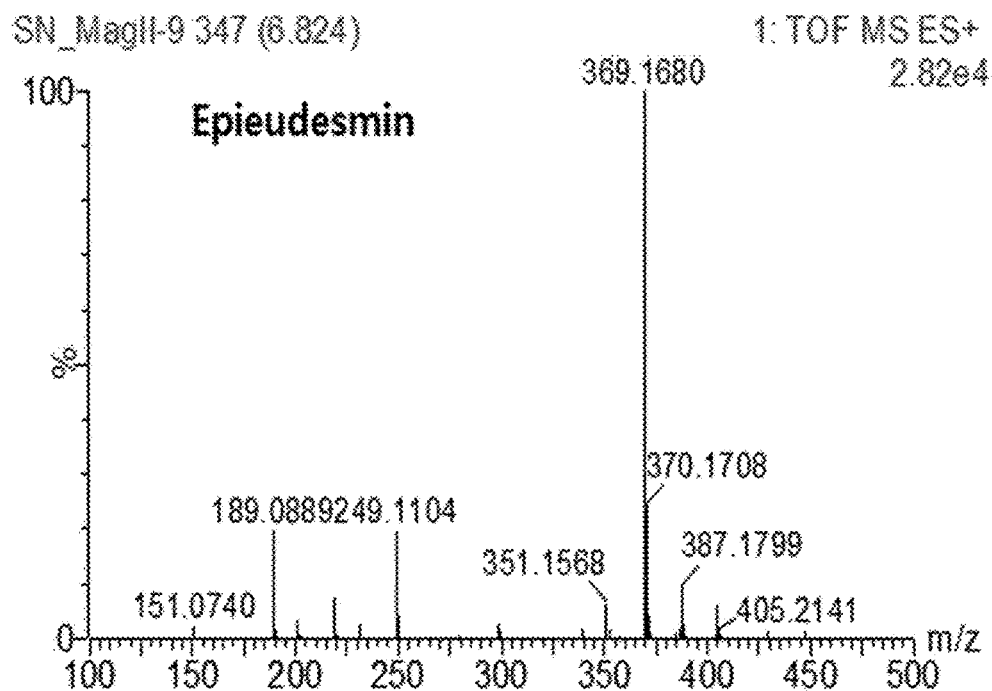
Figure 8E:
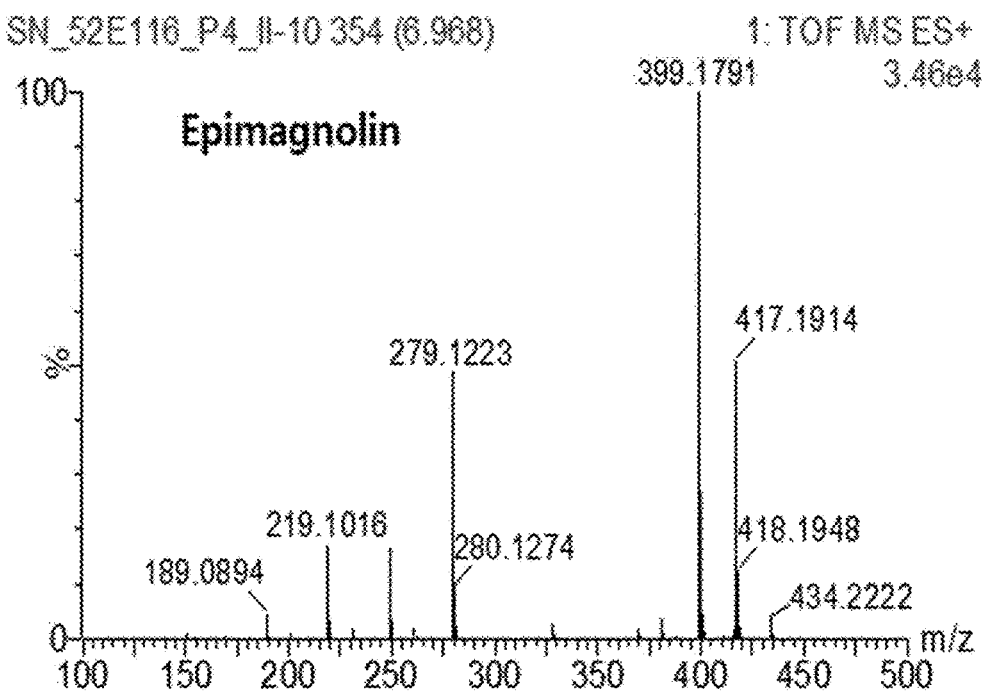
Figure 8F:
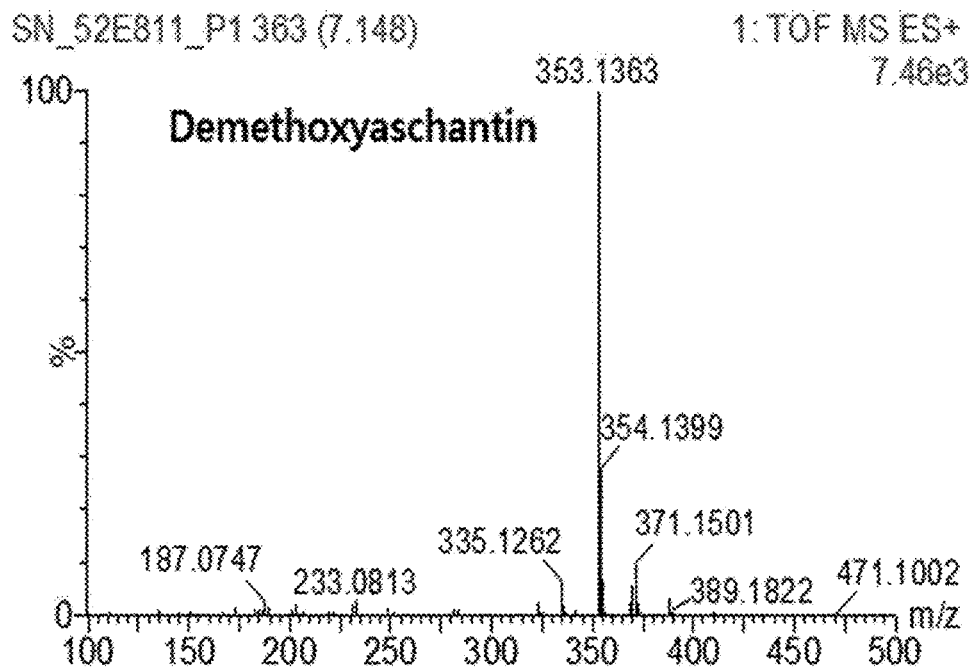
Figure 8G:
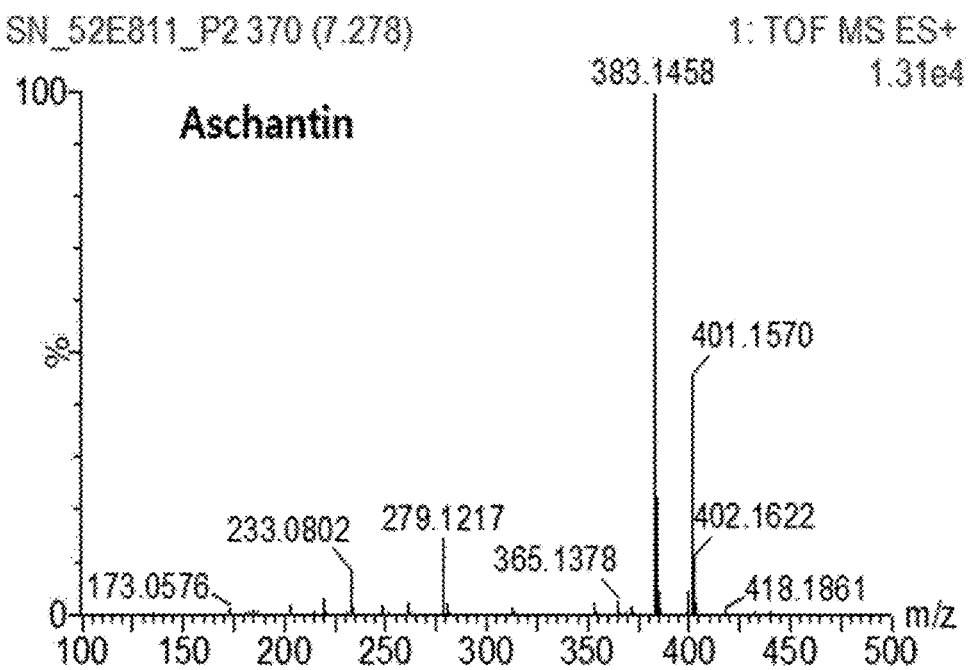
Figure 8H:
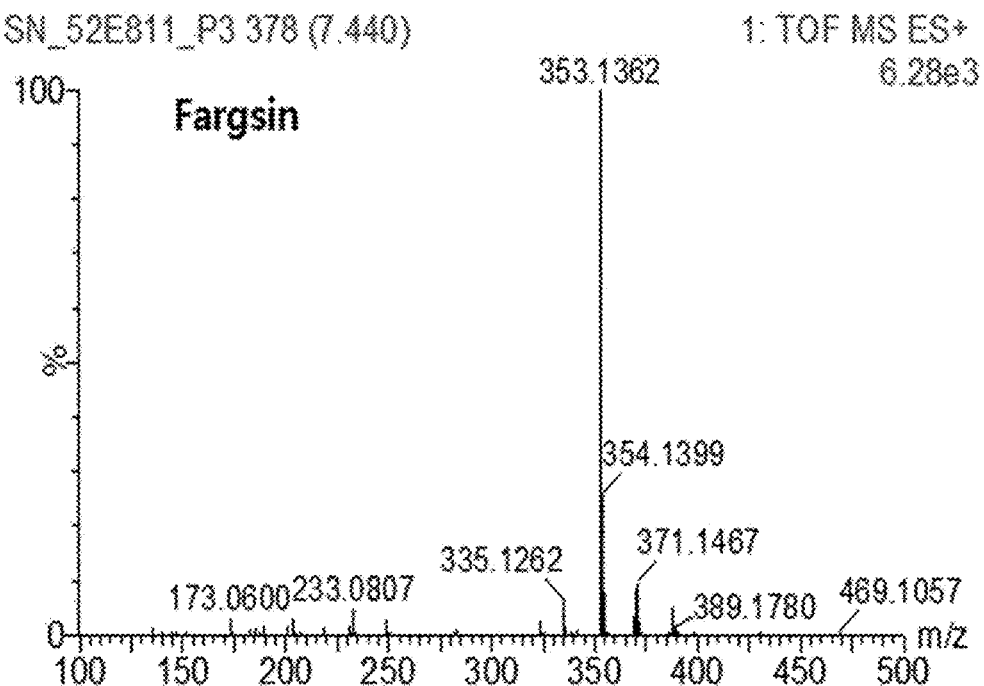

Upon analysis of the ingredients based on the results of Examples 1 to 4, the compounds in the range of from about 6 to 8, shown as a rectangular-shaped box in FIG. 6, were determined to be the ingredients showing the inhibitory effect on cell proliferation. Taken the analyzed result and the result of time-of-flight mass spectrometry (TOFMS) analysis together, eight ingredients predicted to inhibit cell proliferation in the *Magnoliae Flos* extract and fractions thereof were analyzed (FIGS. 7 and 8A to 8H). The ingredients were confirmed to be magnolin, dimethylpinoresinol, demethylliroresinol, epieudesmin, epimagnolin, demethoxyaschantin, aschantin, and fargesin.

Among the isolated ingredients, magnolin was obtained the greatest amount.

Accordingly, magnolin was considered to be the most important ingredient in inducing the cell proliferation inhibition and apoptosis. Therefore, to conduct more specific experiments on the anticancer effects of magnolin, magnolin (HPLC purity of 99.9% or more) was dissolved in DMSO to 1,000-fold higher concentrations of 15 µM, 30 µM, 60 µM, and 100 µM, and each of the samples was stored at −20° C.

Example 6: Verification of the Inhibitory Effect of Magnolin on Cell Proliferation Mouse skin epidermal JB6 Cl41 cells were cultured in Dulbeco's Modified Eagle's Medium (DMEM) containing 10% FBS at 37° C. in a 5% $CO_2$ bioreactor. The cells were subcultured at 80% to 90% confluence and the medium was changed every 2 to 3 days.

The cultured JB6 Cl41 cells ($1\times10^3$ cells) were aliquoted into 96-well plates containing 5% FBS-MEM and cultured for 2 hours at 37° C. in a 5% $CO_2$ bioreactor. Then, each well was added with 20 µL of an aqueous solution of the MTS-based Cell Titer 96, and then, further cultured for 1 hour at 37° C. in a 5% $CO_2$ bioreactor. 25 µL of 10% sodium dodecyl sulfate (SDS) solution was added into each of the wells to stop the reaction. The absorbance at 492 nm was measured to measure the growth of the cells at 0 hour.

While measuring the absorbance at 0 hour, the cells were simultaneously treated with the magnolin samples to final concentrations of 15 µM, 30 µM, and 60 µM, respectively, prepared in Example 5. The cells were cultured for 96 hours while measuring the absorbance at 24 hour intervals. In the experiment, the cell treated with DMSO alone was set as a control.

Figure 9A:
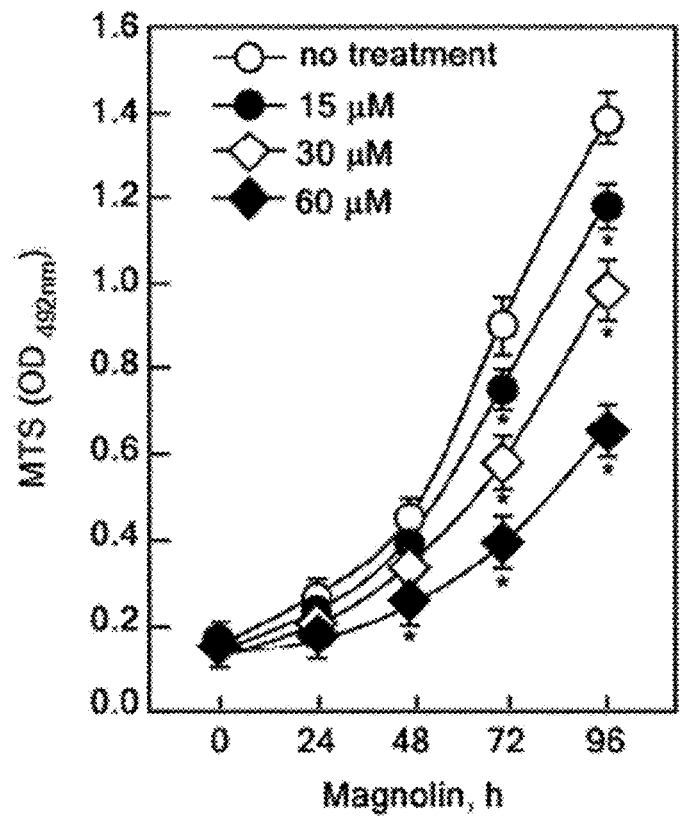

As the result of the experiment, compared with the control treated with DMSO alone, the cell proliferation was inhibited by about 40% when treated with 30 µM magnolin and about 70% when treated with 60 µM magnolin (FIG. 9A).

Additionally, to examine the cytotoxicity of magnolin, the cultured cells ($2\times10^4$ cells) were aliquoted into 96-well plates containing 5% FBS-MEM and cultured overnight. Then, the cells were treated with the magnolin samples to final concentrations of 15 µM, 30 µM, 60 µM, and 100 µM respectively, prepared in the Example 5. The cells were cultured for 48 hours while measuring the absorbance at 24 hour intervals. In the experiment, the cell treated with DMSO alone was set as a control.

Figure 9B:
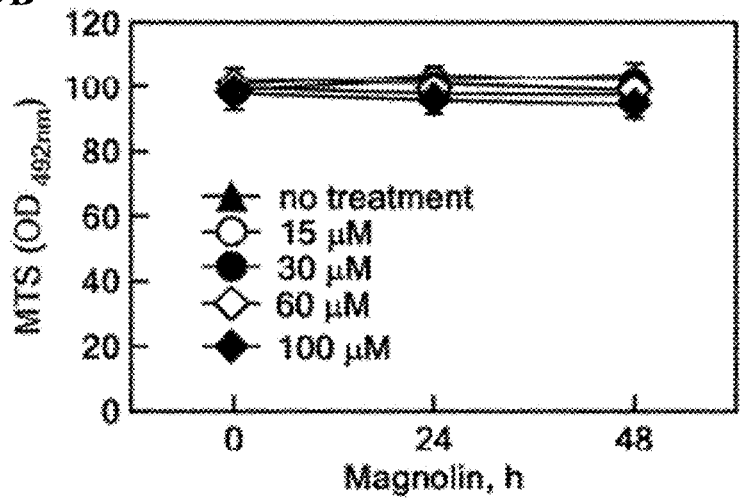

Regarding the cytotoxicity of magnolin, no cytotoxicity was observed even when cells were treated with magnolin at a concentration of 100 µM or higher. Therefore, it was suggested that the magnolin treatment on a subject would not exhibit any harmful actions (FIG. 9B).

Example 7: Verification of the Inhibitory Effect of Magnolin on Cell Cycle Progression In light of the result of Example 6, a hypothesis that the inhibitory effect of magnolin on cell proliferation is achieved by inhibiting cell cycle progression was established. To prove the hypothesis, an experiment was performed as shown below.

The cultured JB6 Cl41 cells ($2\times10^5$ cells) were aliquoted into a cell culture dish with a diameter of 60 mm and they were cultured overnight at 37° C. in a 5% $CO_2$ bioreactor. To observe the cell cycle of the cells under normal cell culture conditions, JB6 Cl41 cells were cultured in a complete cell culture medium for 12 hours and treated with magnolin at final concentrations of 30 μM and 60 μM, respectively. After 12 hours, the cells were treated with trypsin, fixed, and treated with 20 μg/mL of PI at 4° C. for 15 minutes. Then, the cell cycle distribution was analyzed using the flow cytometry (BD FACS Calibur™ Flow cytometery, Franklin Lakes, N.J., USA).

Figure 10A:
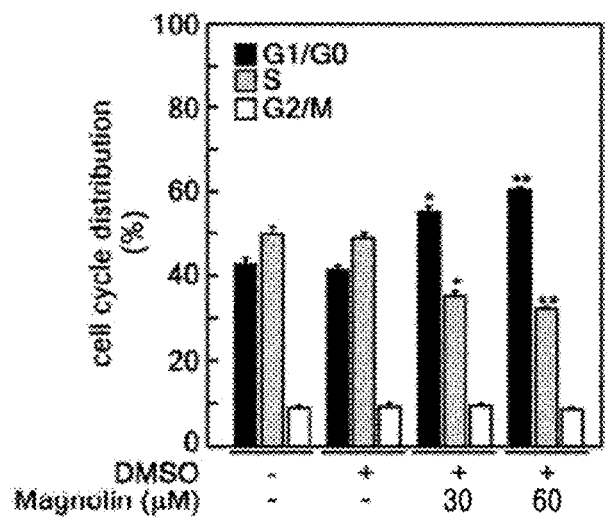
Figure 10B:
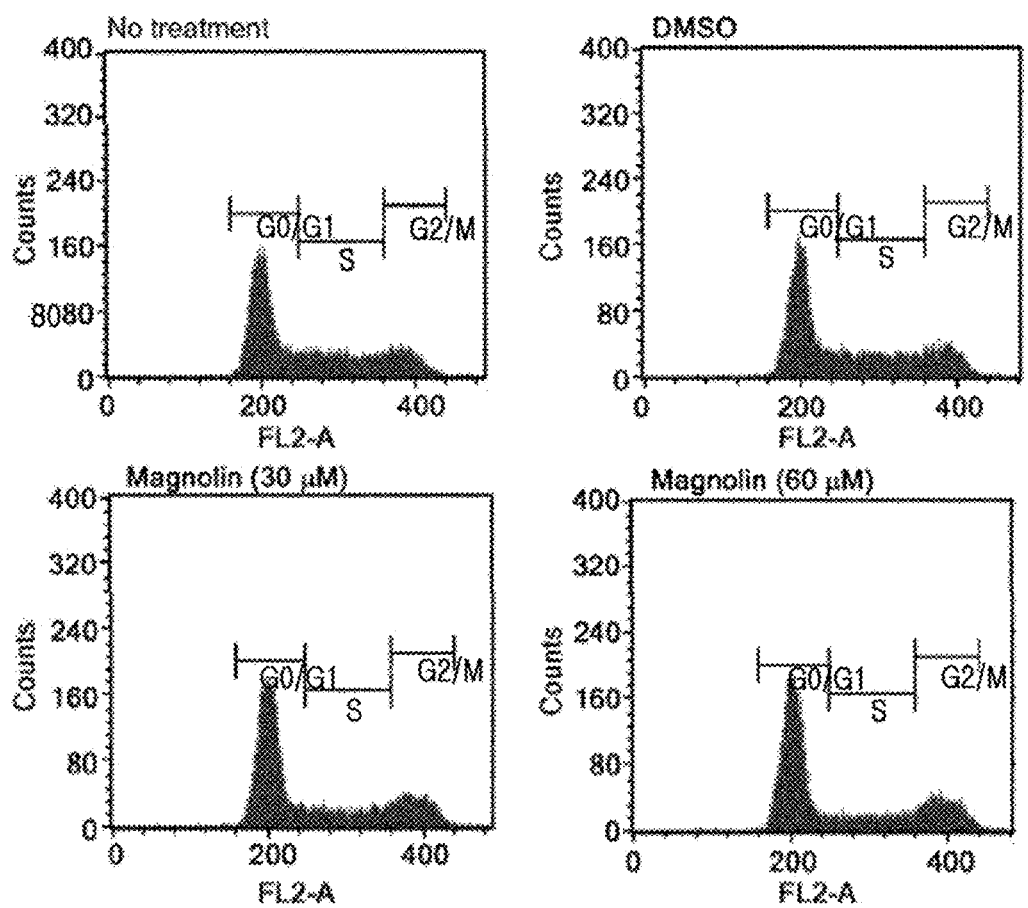

As the result of the experiment, when the cells were treated with 30 μM magnolin, about 55% was distributed in G1/G0 phase while when the cells were treated with 60 μM of magnolin, about 60% was distributed in G1/G0 phase. This showed a considerably increased distribution compared to the case of the control treated with DMS (about 42% distribution in G1/G0 phase). Unlike this, in G2/M cell cycle phase, when treated with magnoin, only a very small increase in distribution was observed compared to the control (FIGS. 10A and 10B).

In contrast, EGF, which is a factor inducing the cell cycle progression, is one of the tumor promoters and is known to induce S cell cycle phase while inhibiting G1/G0 cell cycle phase in general. To observe the action of magnolin on EGF-induced cell cycle progression, an additional experiment was conducted as follows.

The cultured JB6 Cl41 cells ($2 \times 10^5$ cells) were aliquoted into a cell culture dish with a diameter of 60 mm and they were cultured overnight at 37° C. in a 5% $CO_2$ bioreactor. Then, the cells were pretreated with magnolin to final concentrations of 15 μM, 30 μM, and 60 μM, respectively, for 30 minutes. Then, under the presence of magnolin, the cells were stimulated with 1 ng/mL of EGF for 12 hours.

Figure 11A:
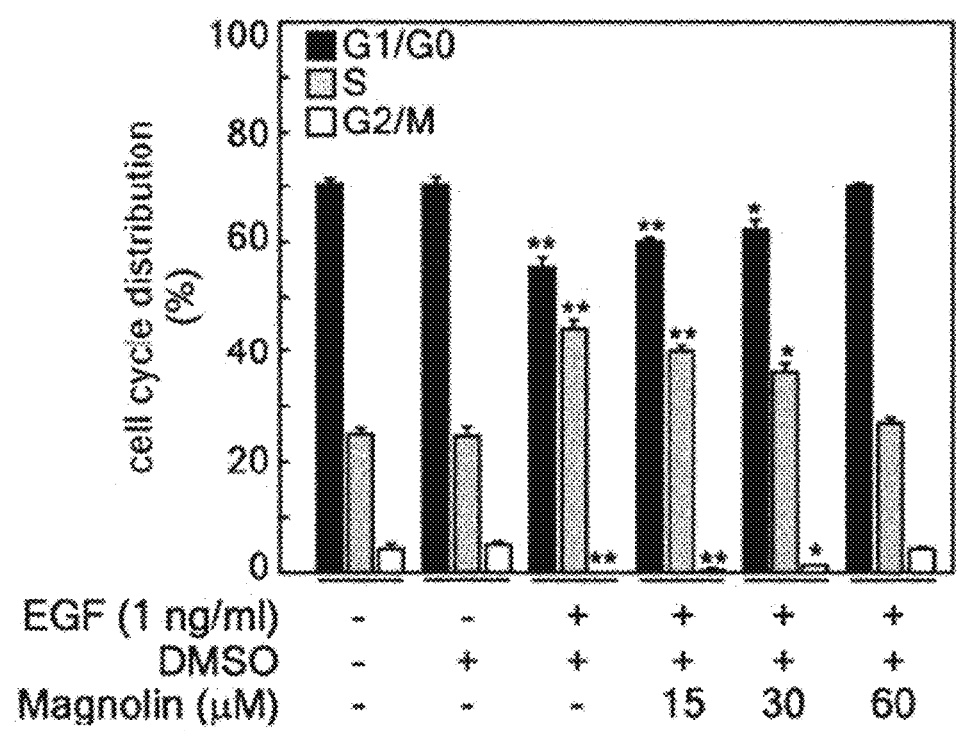
Figure 11B:
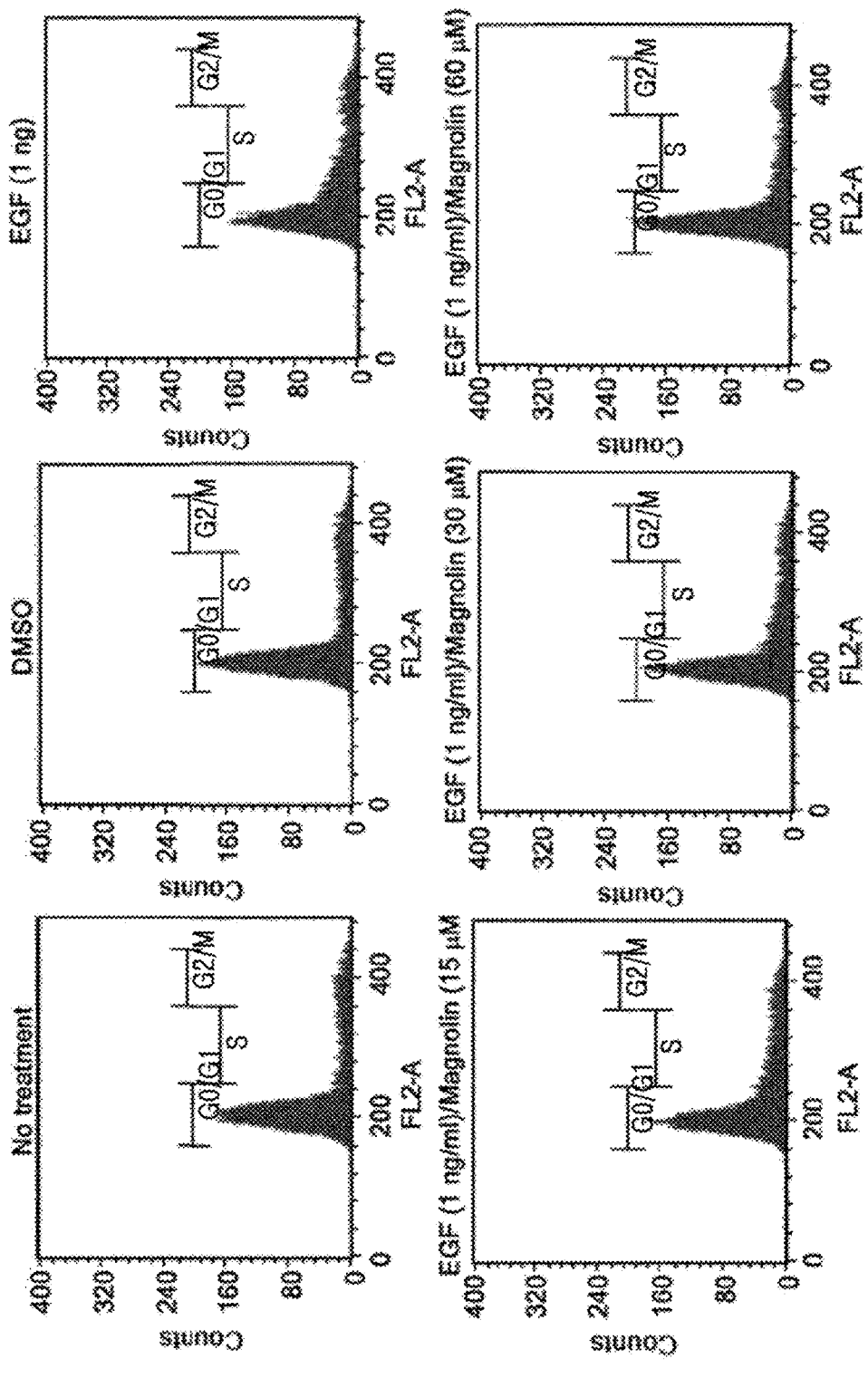

As the result of the experiment, it was confirmed that magnolin treatment considerably interrupts the action of EGF on the cell cycle progression. Specifically, it was confirmed that the effect of EGF on cell cycle was almost completely inhibited when treated with magnolin at a concentration of 60 μM or higher (FIGS. 11A and 11B). Based on the result, it was concluded that magnolin inhibits cell proliferation induced by tumor promoters such as EGF through the inhibition of the G1/S phase on the cell cycle progression.

Example 8: Verification of the Selective Inhibitory Effect of Magnolin on ERKs/RSKs Signaling Pathway-Western Blot Since magnolin was confirmed to inhibit cell proliferation and specifically inhibit the G1/S cell cycle phase induced by EGF in Example 7, the hypothesis that magnolin may inhibit ERKs/RSKs signaling pathway was established, and the experiment below was conducted by Western blot. In the above, ribosomal S6 kinase (RSK), which is one of ribosme kinases, acts as a means for enabling ERK to mediate mitogen-inducing activity signal through phosphorylation.

The cultured JB6 Cl41 cells ($1 \times 10^6$ cells) were aliquoted into a cell culture dish with a diameter of 100 mm and they were cultured overnight. Then, the cells were left for 24 hours in 0.1% FBS-MEM and pretreated with magnolin at concentrations of 15 μM, 30 μM, and 60 μM for 30 minutes, respectively, and after 30 minutes, co-treated with EGF and magnolin.

The proteins were extracted from the cultured JB6 Cl41 cells and the samples containing the proteins were analyzed by 8% to 10% SDS-PAGE, and transferred onto polyvinylidene difluoride (PVDF) membranes. The membranes were cultured in a blocking buffer containing 5% skim milk. Then, Western blot was performed using specific antibodies for phospho-MEK (MAPK (mitogen-activated protein kinase)/ERK kinase), total-MEK, phospho-ERK, total-ERK, phospho-RSK, total-RSK, phospho-Akt, total-Akt, phospho-p38 kinase, total-p38 kinase, phospho-JNK (c-Jun N-terminal kinase), and total-JNK (all the antibodies obtained from Cell Signaling Technology, Beverly, Mass., USA). In particular, β-actin (Santa Cruz, Calif., USA) was used as a control and the Western blot was visualized with an enhanced chemiluminescence detection system (Amersham Biosciences, Piscataway, N.J., USA) using the Chemidoc XRS imager system (Bio-Rad Laboratories, Hercules, Calif., USA).

Figure 12A:
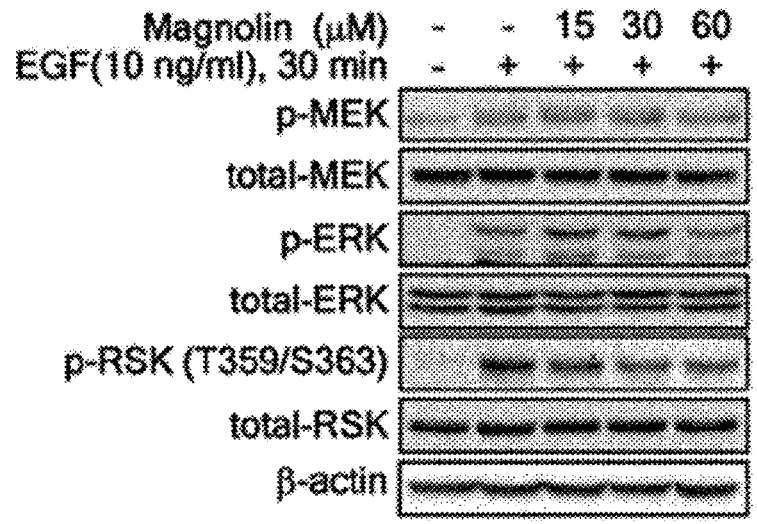
Figure 12B:
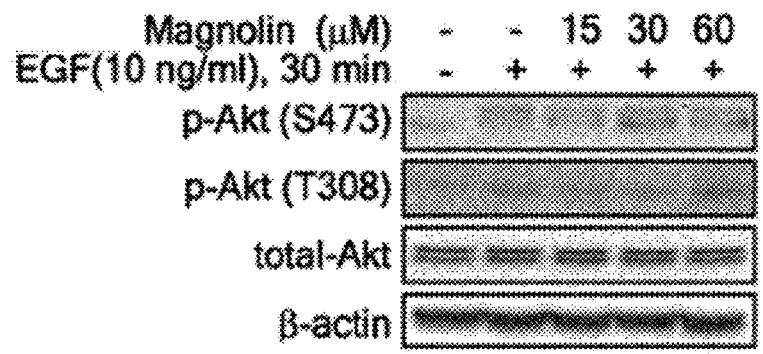
Figure 12C:
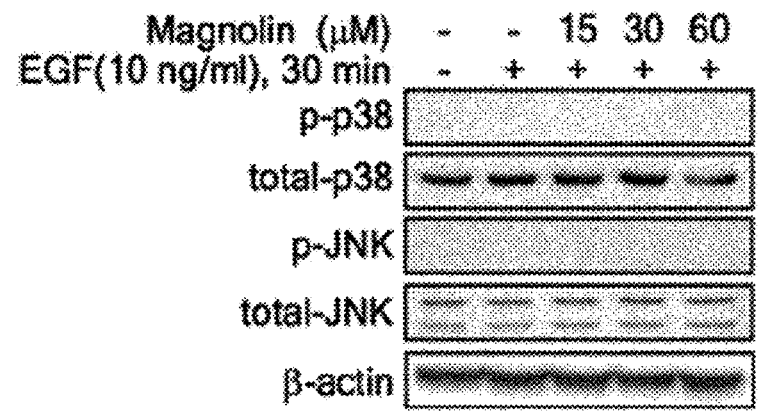

As the result of the experiment, although magnolin showed a feature of interrupting phosphorylation at Thr359/Ser363 of RSKs (FIGS. 12A and 12F), magnolin appeared not to be involved in the phosphorylations of MEK, Akt, p38 kinase, and JNKs (FIGS. 12A to 12C).

Figure 12D:
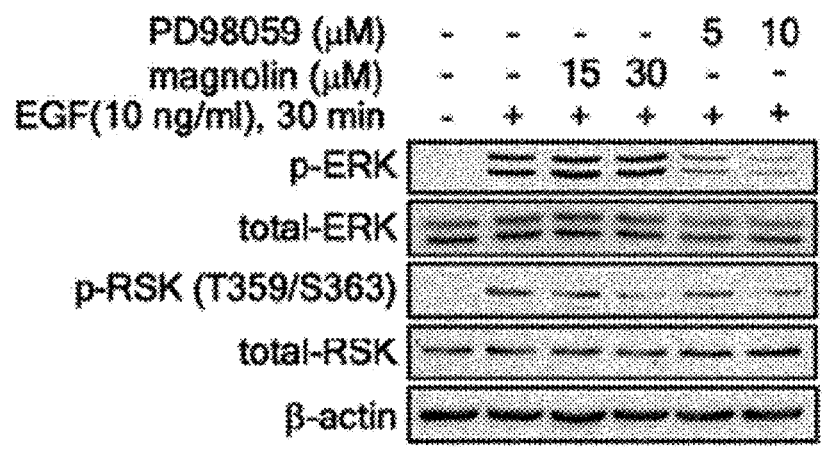
Figure 12E:
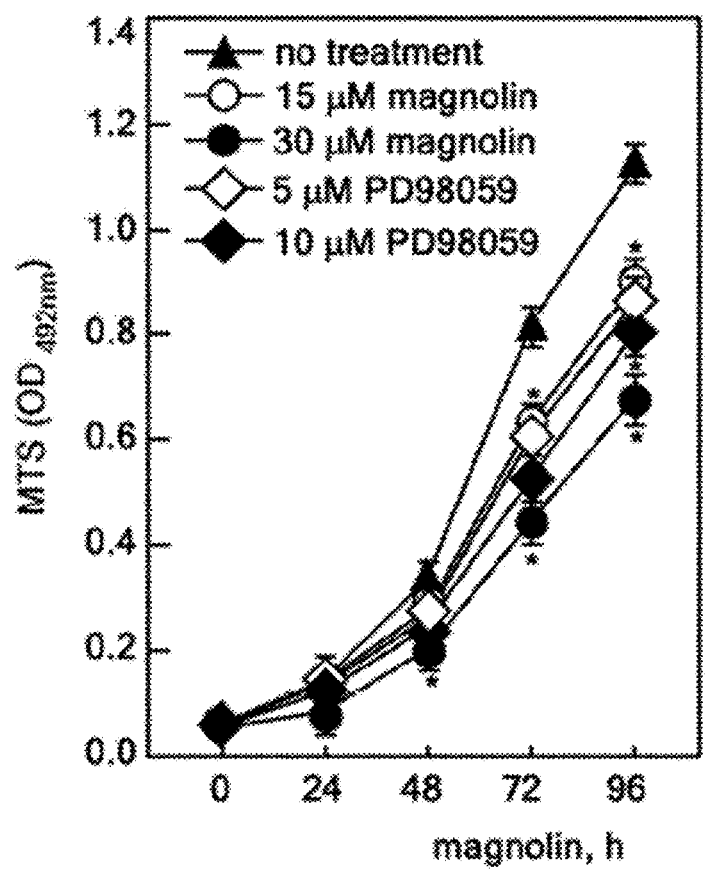
Figure 12F:
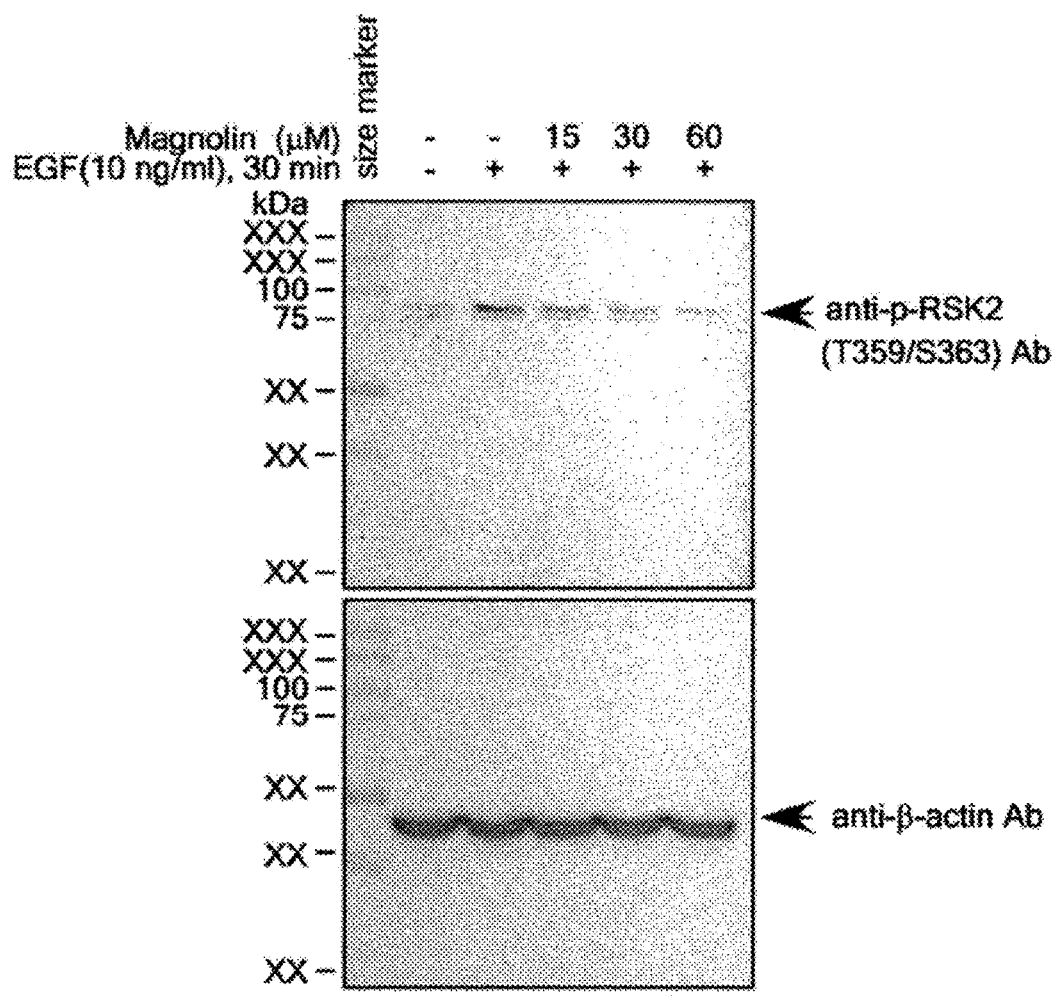

To confirm whether the action of magnolin, which interrupts phosphorylation at Thr359/Ser363 of RSKs, was selective in MEKs/ERKs signaling pathways or not, the action was compared by conducting an experiment on the phosphorylation of ERKs and RSKs by treatment with PD98059, an MEK1/2 inhibitor. As a result, it was confirmed that PD98059 interrupts ERK1/2 phosphorylation at Thr202/Tyr204. In contrast, it was confirmed that magnolin does not interrupt the phosphorylation, whereas RSKs phosphorylation at Thr359/Ser363 were all inhibited by magnolin and PD98059, respectively (FIG. 12D). FIG. 12E shows the inhibition of cell proliferation in JB6 Cl41 cells, which were independently treated with magnolin and PD98059, respectively. Based on the result described above, it was determined that magnolin selectively inhibits the activities of ERKs.

Example 9: Verification as to Whether Magnolin Targets Erk1 and Erk2-In Vitro Kinase Analysis and Computational Docking In Example 8, it was confirmed that magnolin inhibits the activities of ERK (ERK1 and ERK2) and the experiment below was conducted to observe this in more detail.

A truncated RSK2 protein containing the amino acid at position 328 to the amino acid at position 740 (His-RSK-328-740) was purified using Ni-NTA agarose beads (Qiagen Korea Ltd., Seoul, Korea) (Left panel on FIG. 13A) and an in vitro-kinase analysis was performed using active ERK and His-RSK2-328-740 proteins. Specifically, in the in vitro-kinase analysis, 20 μL of the purified sample was treated with 20 ng of active ERK1 or ERK2, 100 ng of RSK2, and 100 μM of cold-ATP, and 3.75 μM, 7.5 μM, 15 μM, 30 μM, and 60 μM of magnolin, respectively. Then, the kinase reaction was performed for 30 minutes at 30° C. The reaction was stopped by adding 6×SDS-sample buffer followed by boiling. Upon termination of the reaction, the resultant was visualized by Western blot.

Figure 13A:
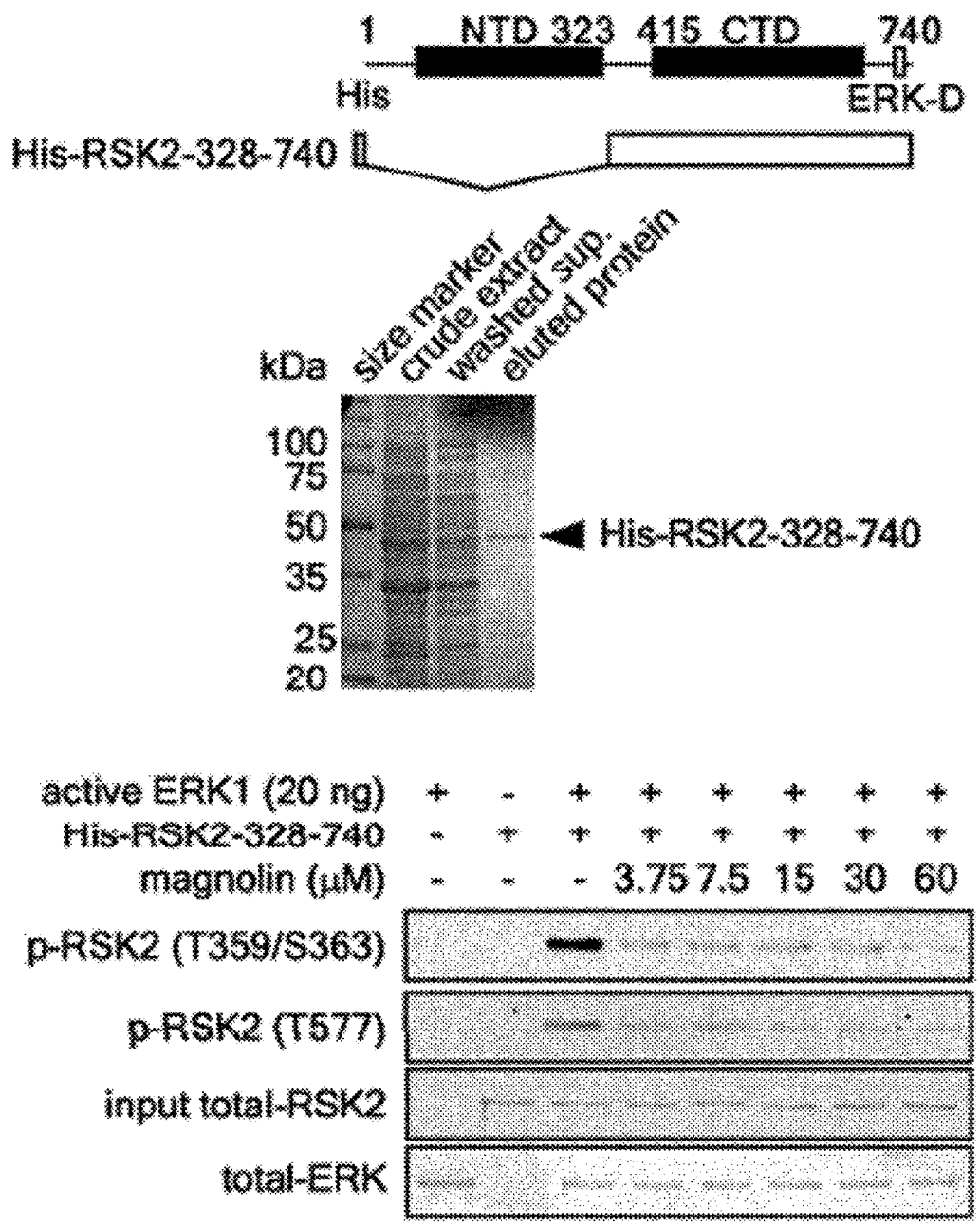

As the result of the experiment, it was confirmed that ERK1-mediated RSK2 phosphorylation at Thr359/Ser363 and Thr577 was inhibited by about 90% by magnolin (Right panel on FIG. 13A). Taken together with the result of Example 8, the result shows that magnolin inhibits the activities of ERK1 and ERK2.

After the experiment, computational docking of magnolin with ERK1 and ERK2 was conducted. For flexible docking of magnolin and ERKK1 or ERK2 by the standard precision (SP) mode, the crystal structures of ERK1 (2ZOQ) and ERK2 (1WZY) were obtained from the protein data bank (PDB) (htt://www.rcsb.org/pdb/home/home.do).

Figure 13C:
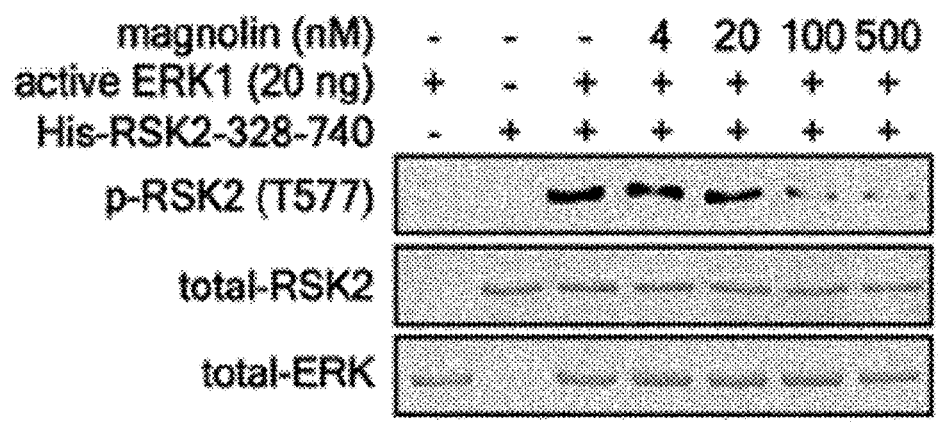
Figure 13D:
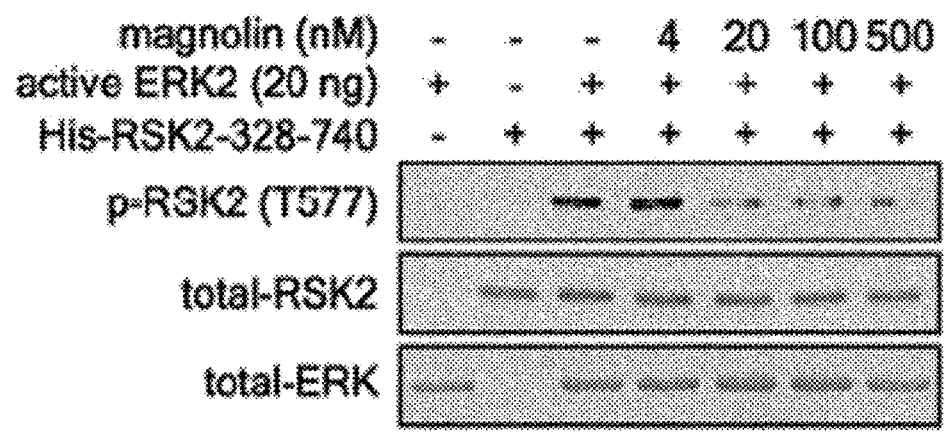

As the result of the computational docking, it was observed that magnolin forms hydrogen bonds with Lys168 of ERK1 (Left panel on FIG. 13B) and Met108 and Lys54 of ERK2 (Right panel on FIG. 13B), respectively. Further, it was confirmed that magnolin in the active pocket of ERK1 or ERK2 was completely different in molecular structure and binding angle. The docking scores of magnolin at the active pockets of ERK1 and ERK2 were −0.7 and −6.68, respectively. Further, to measure the $IC_{50}$ value on the activity of ERK1 or ERK2, the in vitro-kinase analysis was performed. The $IC_{50}$ value of magnolin on ERK1 activity was about 87 nM (FIG. 13C) and on ERK2 activity was 16.5 nM (FIG. 13D).

Figure 13E:
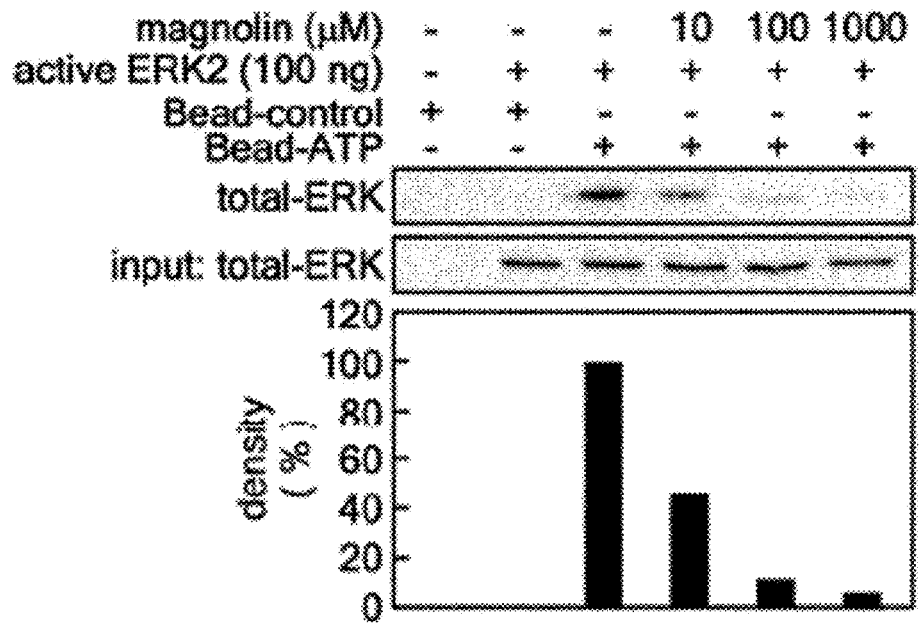

Then, to confirm whether magnolin was competitive with ATP or not, a magnolin competition analysis was performed using APT-agarose beads. As the result of the experiment, it was confirmed that an increase in magnolin decreased ERK2 that bind to ATP-agarose beads (FIG. 13E). Accordingly, it was suggested that magnolin inhibits the ERKs/RSKs signaling pathway by competing with ATP in targeting the active site of ERK1 or ERK2 thereby inhibiting cell prolilfeationP.

Example 10: Verification of Inhibitory Effect of Magnolin on ATF1 and AP-1 Transactivation Activities The experiment below was conducted to confirm whether magnolin inhibits phosphorylation of ATF1 (ERKs/RSK2/c-AMP-dependent transcription factor) and c-Jun, a critical component of the activator protein (AP)-1, nuclear localization of phospho-ATF1 and phospho-c-Jun, and transactivation activities of ATF1 and AP-1 complexes.

$1\times10^6$ of the cultured JB6 Cl41 cells were cultured in a cell culture dish with a diameter of 100 mm for overnight. The cells were starved and left for 24 hours, and then pretreated with magnolin at concentrations of 15 μM, 30 μM, and 60 μM of for 30 minutes, and then co-treated with 10 μg/mL of EGF and magnolin for 30 minutes. The proteins were extracted from the cells and visualized by Western blot. On the other hand, the cells were co-transfected with pGAL4-ATF1-expressing plasmids and p5xGal4-luciferase reporter plasmids, and then cultured for 12 hours. The cells were pretreated with magnolin for 30 minutes, and co-treated with EGF and magnolin for 6 hours. Then, the cell culture was stopped and the activity of firefly luciferase was measured using the VIXTOR X3(PerkinElmer).

Figure 14A:
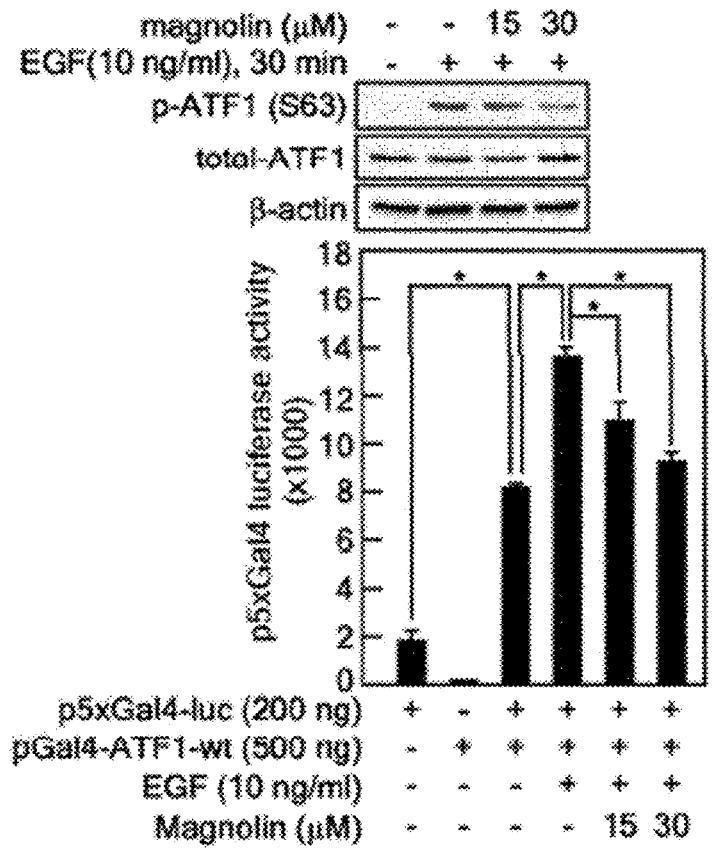
Figure 14B:
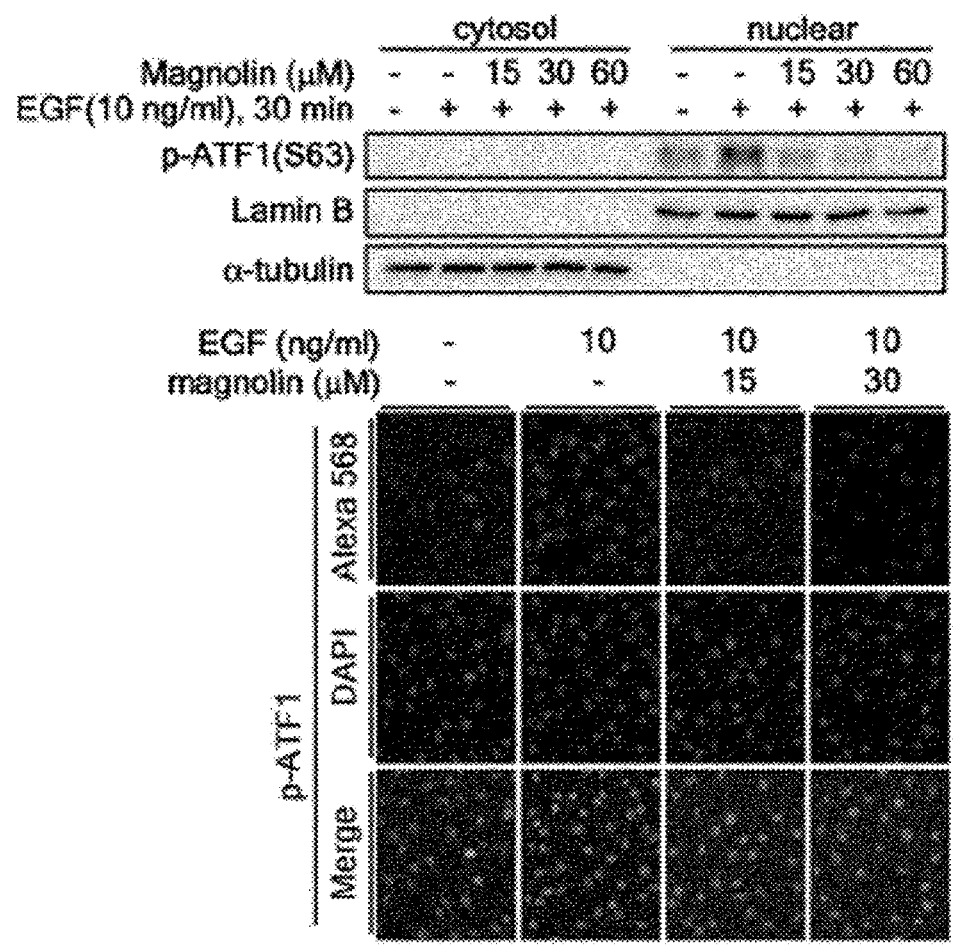

As the result of the experiment, it was confirmed that EGF-induced ATF1 phosphorylation at Ser63 was inhibited by magnolin (FIG. 14A). Additionally, when co-treated with EGF and magnolin, it was confirmed that ATF1 transactivation activity that had been increased by EGF stimulation was inhibited by magnolin in the same manner as the inhibition of ATF1 phosphorylation by magnolin from above. Further, as the result of Western blot and immunocytofluorescence analysis, it was observed that the nuclear phospho-ATF1 protein level induced by EGF was decreased by magnolin when co-treated with EGF and magnolin (FIG. 14B).

Figure 14C:
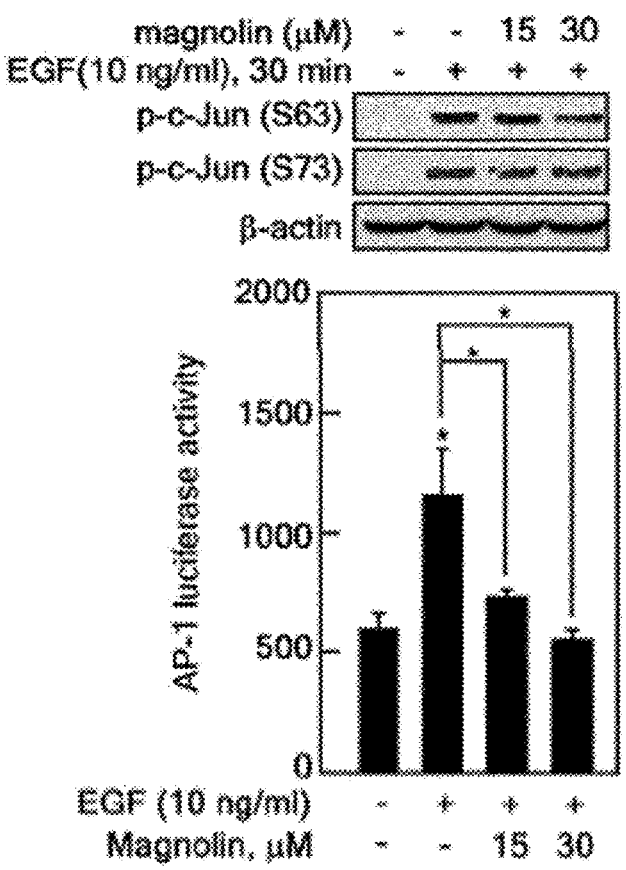
Figure 14D:
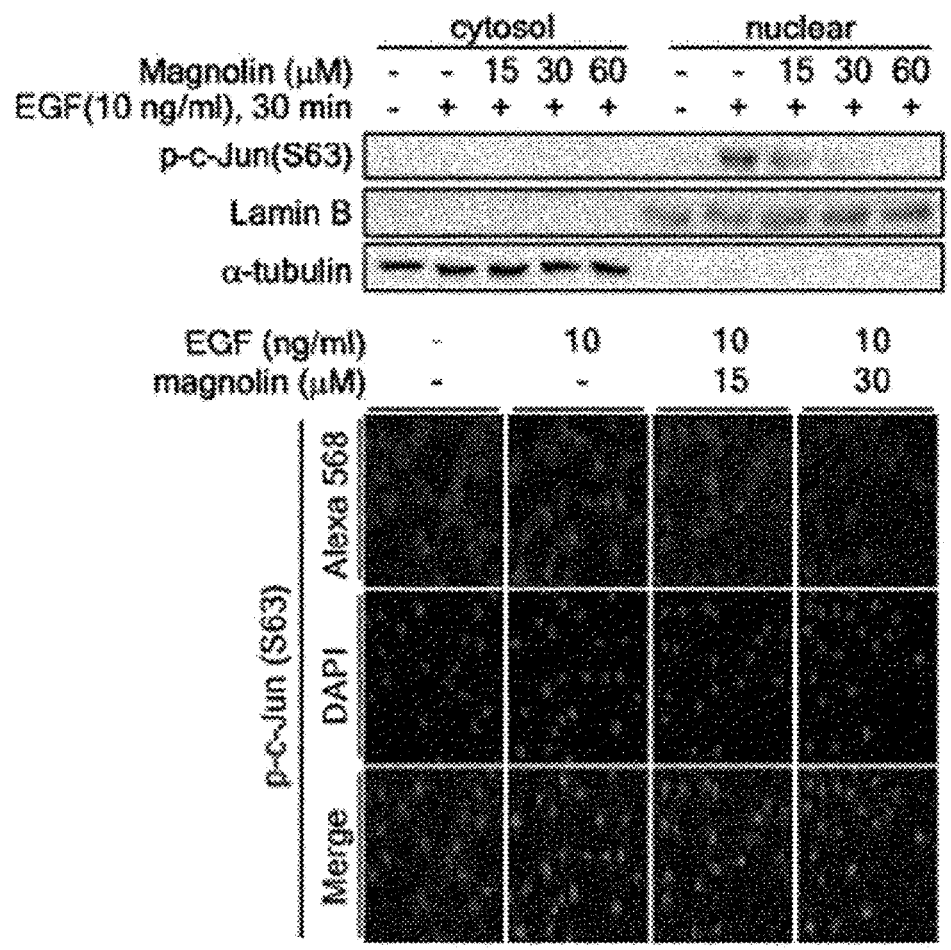

Further, when co-treated with EGF and magnolin, EGF-induced c-Jun phosphorylation at Ser63 and Ser73 and AP-1 transactivation activity were inhibited by magnolin (FIG. 14C), and nuclear phspho-c-Jun increased by EGF stimulation was decreased by magnolin (FIG. 14D). From the results above, it was confirmed that magnolin inhibits AP-1 transactivation activities and inhibits the activities of ERKs, thus interrupting cell proliferation.

Example 11: Verification as to Whether Magnolin has an Inhibitory Effect on EGF-Induced Cell Transformation-Anchorage-Independent Cell Transformation Assay To confirm whether magnolin acts to inhibit cell transformation induced by tumor promoters such as EGF, the anchorage-independent cell transformation analysis was performed as below.

JB6 Cl41 cells ($8\times10^3$ cells) present in 1 mL of 0.3% Basal Medium Eagle (BME) agar containing 10% FBS and magnolin in concentrations of 15 μM, 30 μM, and 60 μM, respectively, were exposed to 10 ng/mL of EGF, maintained at 37° C., and cultured in a 5% $CO_2$ bioreactor for 14 days. Then, the number and size of the colonies were counted using an ECLIPSE Ti inverted microscope and the NIS-Elements AR (V. 4.0) computer software program (NIKON Instruments Korea, Seoul, Korea).

Figure 15:
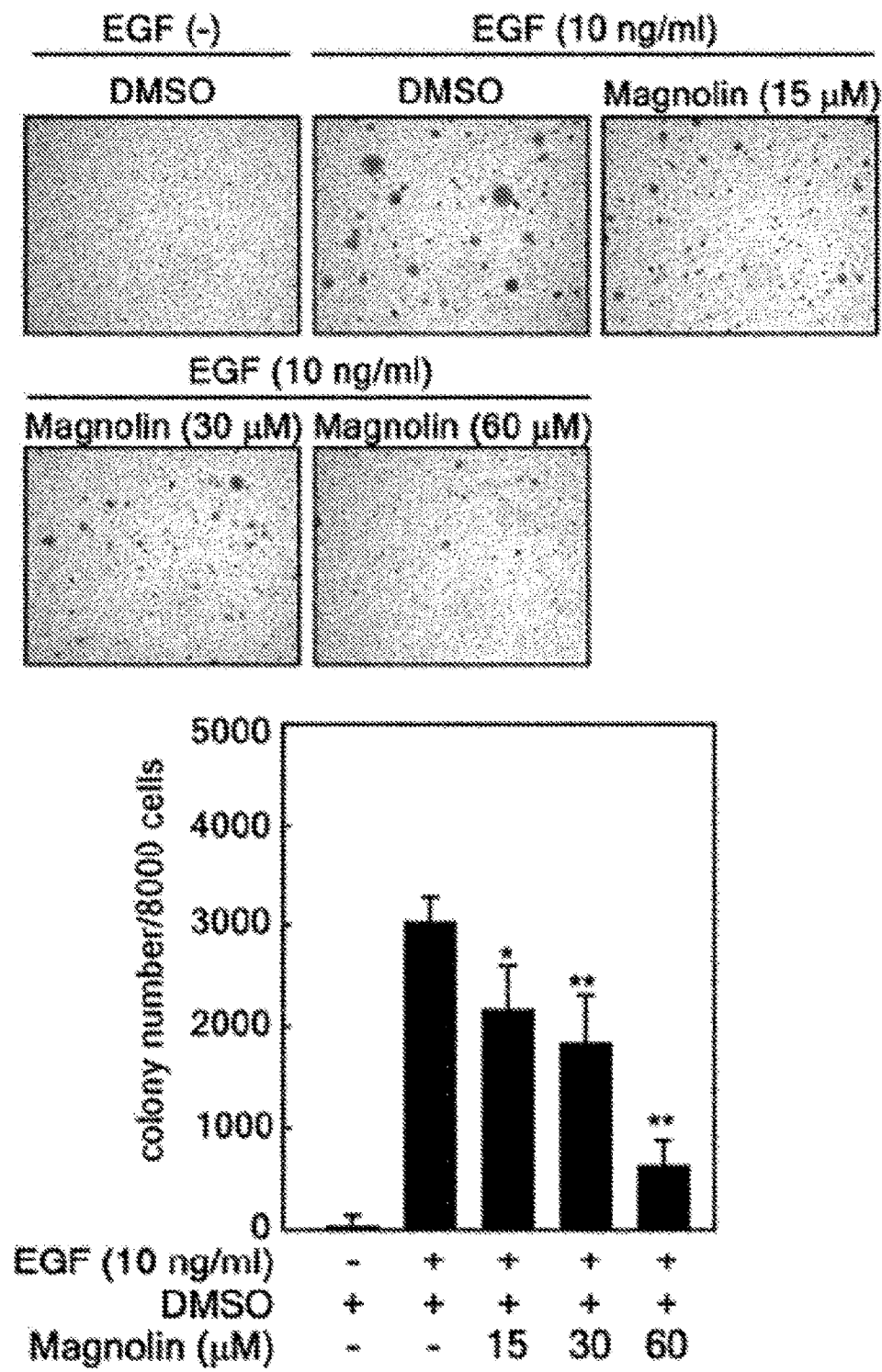
FIG. 15 shows the inhibitory effect of magnolin on EGF-induced cell transformation by an anchorage-independent cell transformation analysis.

As the result of the experiment, it was confirmed that the treatment with 30 μM magnolin inhibited the anchorage-independent cell transformation by about 40% while the treatment with 60 μM magnolin inhibited the anchorage-independent cell transformation by about 75% (FIG. 15).

In contrast, to confirm whether magnolin selectively inhibits Ras/ERKs signaling pathway in cell proliferation and transformation, the experiment shown below was performed using A549 having constitutive mutation of Ras ($Ras^{G12V}$) and H226 having Ras-wt.

Figure 16A:
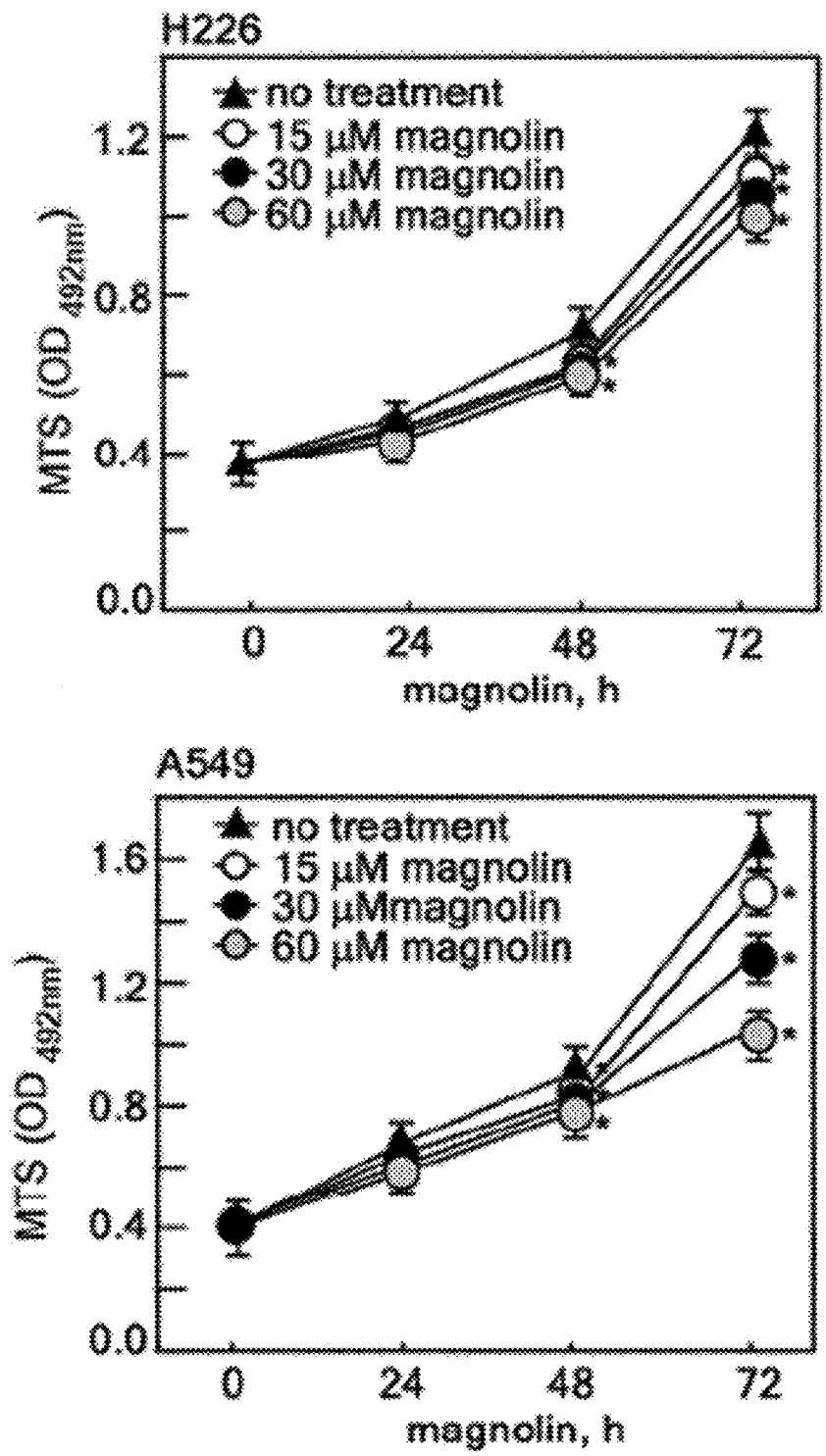

H226 human lung cancer cells ($2\times10^3$ cells) harboring Ras-wt and A549 human lung cancer cells ($2\times10^3$ cells) harboring $Ras^{G12V}$, mutant activating factor, were aliquoted into 96-well plates, respectively, and treated with magnolin at concentrations of 15 μM, 30 μM, and 60 μM. The cells were cultured for 96 hours at 24 hour intervals and the cell proliferation was measured. As the result of the experiment, it was confirmed that magnolin inhibited cell proliferation in A549 cells more significantly compared with H226 cells (FIG. 16A).

Figure 16B:
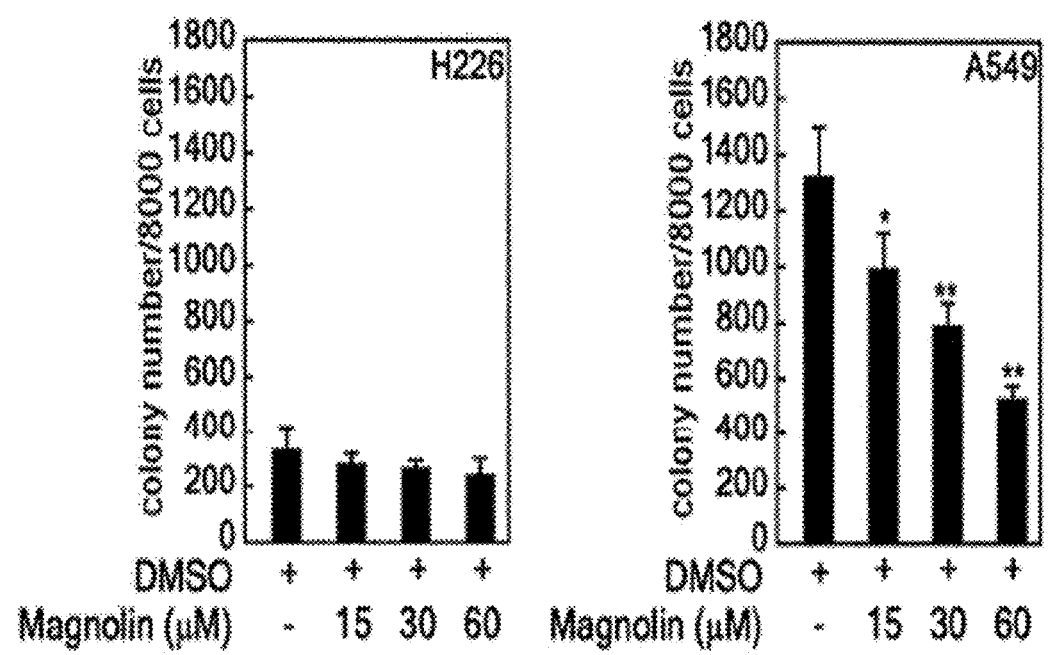
Figure 16C:
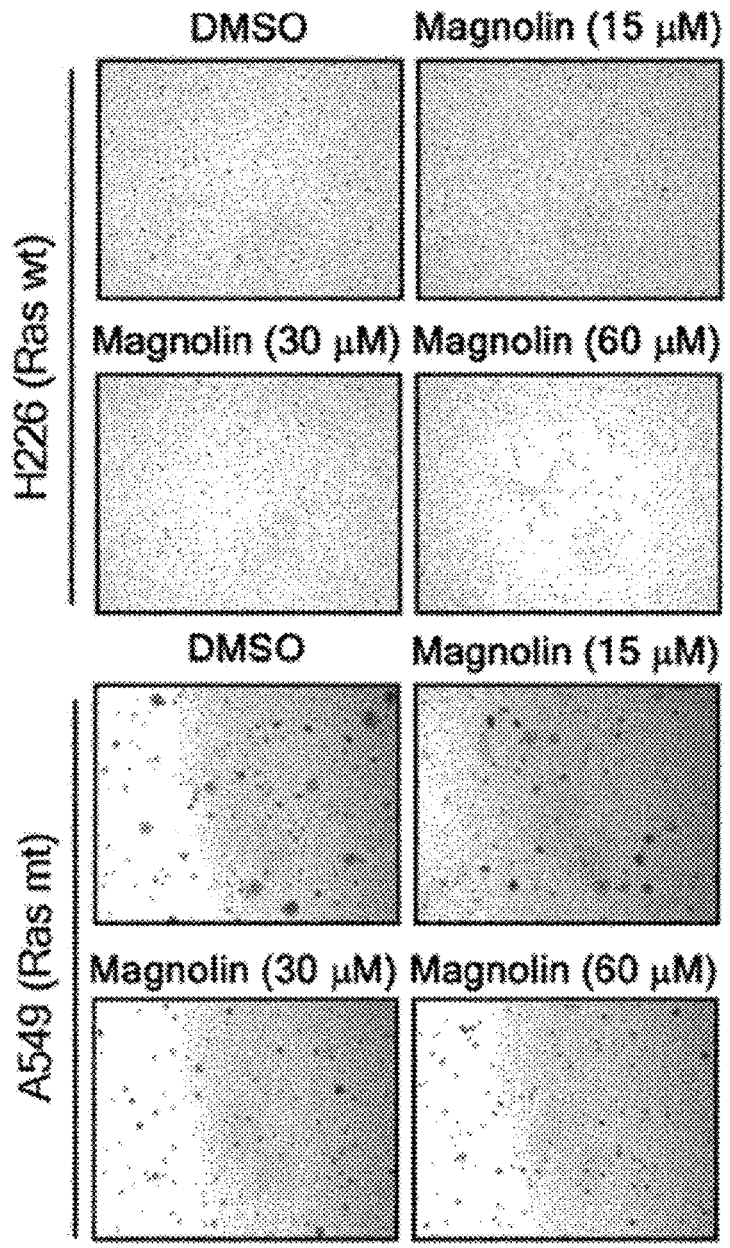

Further, H226 cells ($8\times10^3$ cells) having Ras-wt and A549 cells ($8\times10^3$ cells) having $Ras^{G12V}$ were cultured in 1 mL of 0.3% DMEM agar containing 10% FBS and 15 μM, 30 μM, and 60 μM of magnolin, respectively, maintained at 37° C., and cultured in a 5% $CO_2$ bioreactor for 10 days. As the result of counting the number and size of the cell colonies using an ECLIPSE Ti inverted microscope and the NIS-Elements AR (V. 4.0) computer software program, it was observed that an anchorage-independent colony growth of A549 cells was inhibited by magnolin. However, it was confirmed that H226 cells did not grow well under soft agar (FIGS. 16B and 16C).

In order to confirm the experimental results more precisely, NIH3T3 cells stably expressing mock or $Ras^{G12V}$ were used to perform an additional experiment in the same manner as described above.

Figure 17A:
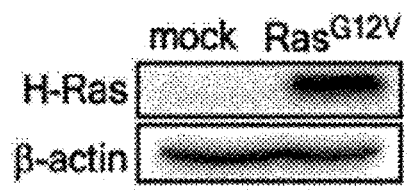
Figure 17B:
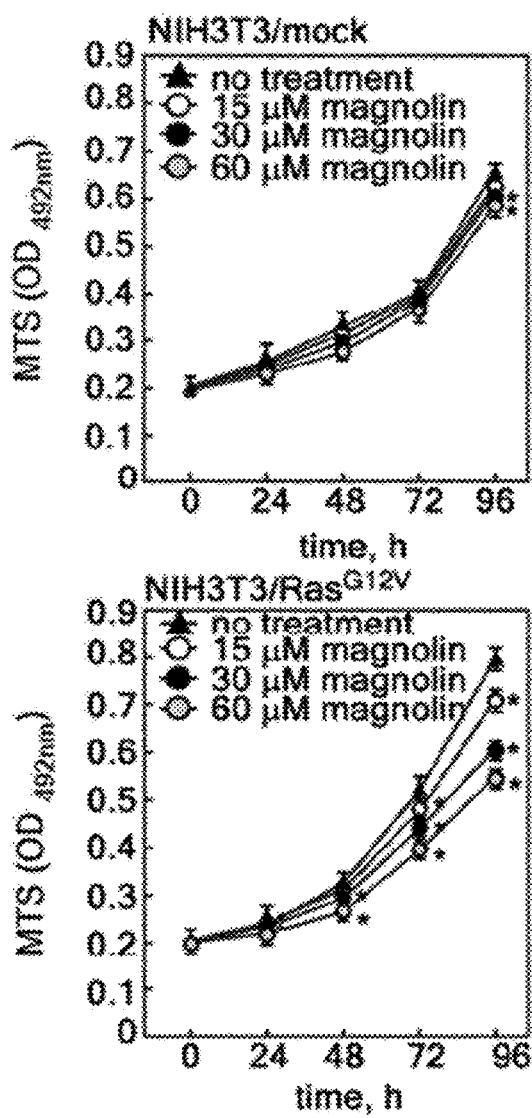
Figure 17C:
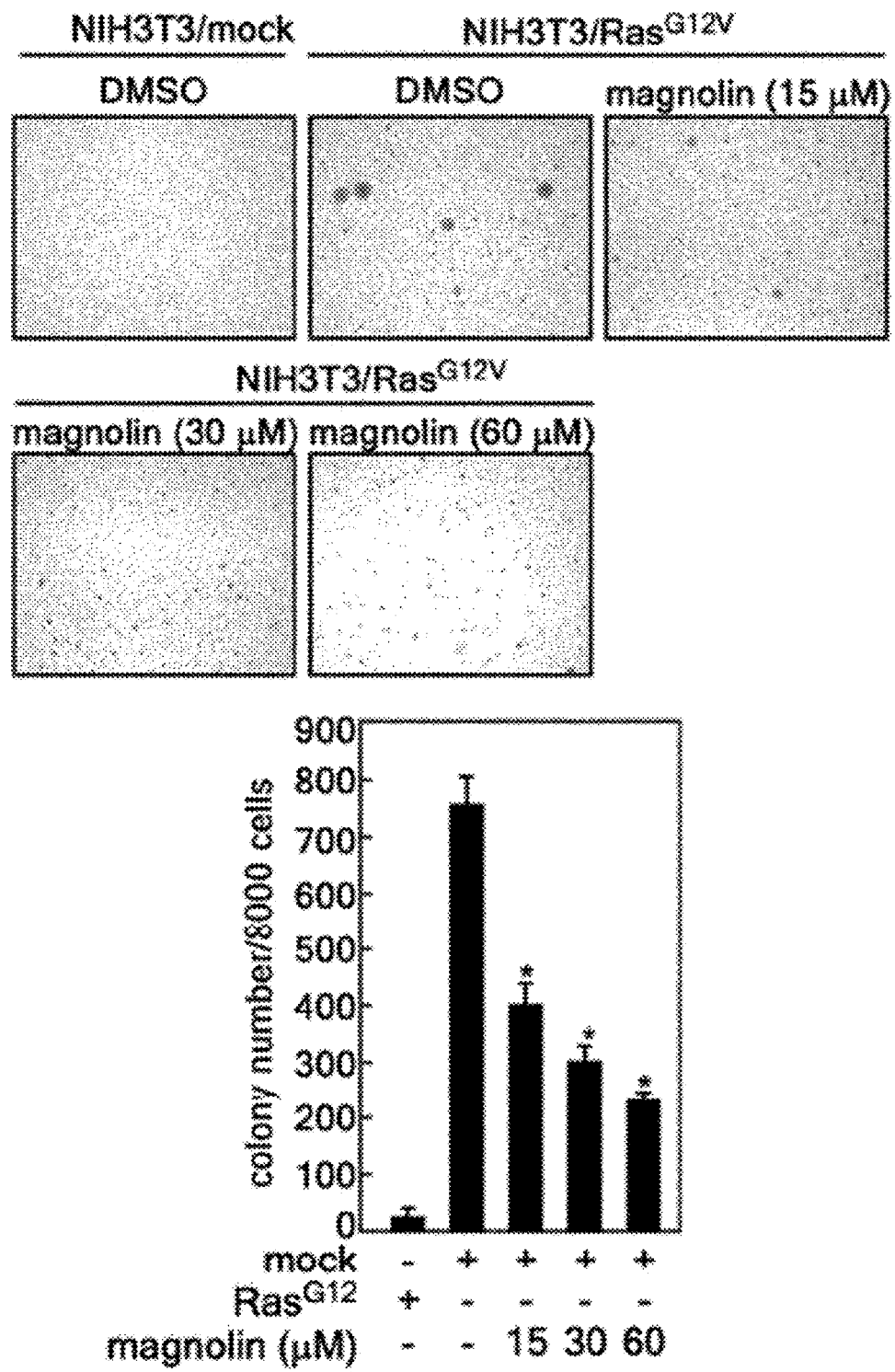

As the result of the experiment, when compared with the NIHT3T cells expressing mock, the inhibition of cell proliferation by magnolin was more sensitive in NIH3T3 cells expressing $Ras^{G12V}$ (FIGS. 17A and 17B). Further, whereas an anchorage-independent colony growth was not observed in the NIH3T3 cells expressing the mock, the NIH3T3 cells expressing $Ras^{G12V}$ showed an anchorage-independent colony growth, thus suggesting the transformation of the cells. It was confirmed that an anchorage-independent growth was inhibited when NIH3T3 cells expressing the Ras$^{G12V}$ were treated with magnolin (FIG. 17C).

Taken the results together, it was confirmed that magnolin, which targets ERK1 and ERK2 active pockets, inhibits Ras/ERK/RSK2-mediated downstream signaling pathways including ATF1 and AP-1, resulting in the inhibition of cell proliferation and transformation induced by tumor promoters such as EGF.

In the specification, the detailed disclosure may be omitted if they are adequately recognized and inferred by one of ordinary skill in the art of the present invention. The present invention may be embodied in other specific forms without modifying the technical concepts or essential characteristics of the present invention other than the detailed Examples disclosed in the specification. Accordingly, the present invention may be practiced in different methods other than detailed explanations and examples disclosed in the specification, and may be understood by one of ordinary skill in the art of the present invention.

The invention claimed is:

1. A method for treating lung cancer, comprising administering a pharmaceutical composition comprising a compound extracted from *Magnoliae Flos* of Chemical Formula 1 or a pharmaceutically acceptable salt thereof as an active ingredient:

[Chemical Formula 1]

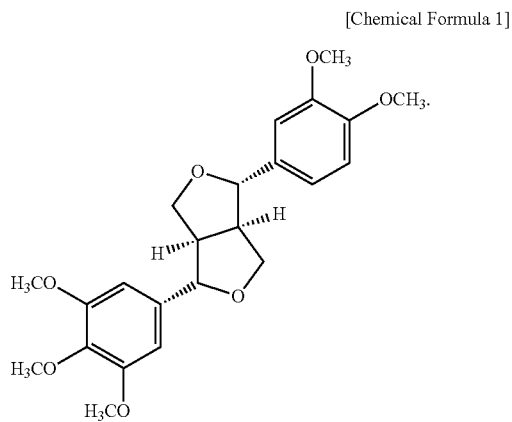

2. The method of claim 1, wherein the composition comprising the compound extracted from *Magnoliae Flos* further comprises one or more compounds selected from the group consisting of dimethylpinoresinol, dimethylliroresinol, epieudesmin, epimagnolin, demethoxyaschantin, aschantin, and fargesin.

3. The method of claim 1, wherein the compound of Chemical Formula 1 in the pharmaceutical composition is in a concentration range from 1 µM to 100 µM.

4. The method of claim 1, wherein the composition comprising the compound extracted from *Magnoliae Flos* treats lung cancer by controlling extracellular signal-regulated kinase (ERK) activity and inhibiting a proliferation of tumor cells.

5. A method for ameliorating lung cancer, comprising administering a health functional food composition comprising a compound extracted from *Magnoliae Flos* of Chemical Formula 1 or a sitologically acceptable salt thereof as an active ingredient:

[Chemical Formula 1]

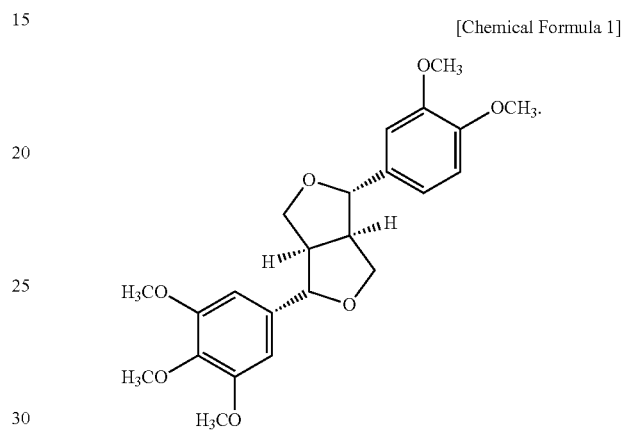

6. A method for treating lung cancer, comprising administering a pharmaceutical composition comprising a chloroform fraction of *Magnoliae Flos* containing magnolin as an active ingredient.

7. The method of claim 6, wherein the composition further comprises one or more compounds selected from the group consisting of dimethylpinoresinol, dimethylliroresinol, epieudesmin, epimagnolin, demethoxyaschantin, aschantin, and fargesin.

8. The method of claim 6, wherein the *Magnoliae Flos* chloroform fraction containing magnolin of the pharmaceutical composition is in a concentration range from 2 µg/mL to 250 µg/mL.

9. A method for ameliorating lung cancer, comprising administering a health functional food composition comprising a chloroform fraction of *Magnoliae Flos* containing magnolin as an active ingredient.

* * * * *